(12) United States Patent
Olive et al.

(10) Patent No.: US 8,318,166 B2
(45) Date of Patent: Nov. 27, 2012

(54) LIGANDS OF HVEM FOR TREATING HEMATOLOGIC MALIGNANCIES

(75) Inventors: Daniel Olive, Marseilles (FR); Alemseged Truneh, Sudbury, MA (US); Christine Pasero, Marseilles (FR)

(73) Assignees: Daniel Olive, Marseilles (FR); Alemseged Truneh, Sudbury, MA (US)

( * ) Notice: Subject to any disclaimer, the term of this patent is extended or adjusted under 35 U.S.C. 154(b) by 0 days.

(21) Appl. No.: 12/602,539

(22) PCT Filed: Jun. 2, 2008

(86) PCT No.: PCT/EP2008/056756
§ 371 (c)(1),
(2), (4) Date: Dec. 1, 2009

(87) PCT Pub. No.: WO2008/145754
PCT Pub. Date: Dec. 4, 2008

(65) Prior Publication Data
US 2010/0196386 A1    Aug. 5, 2010

(30) Foreign Application Priority Data
Jun. 1, 2007  (WO) .................. PCT/IB2007/053425

(51) Int. Cl.
*A61K 39/395*    (2006.01)
(52) U.S. Cl. .................................................... 424/141.1
(58) Field of Classification Search .................. None
See application file for complete search history.

(56) References Cited

U.S. PATENT DOCUMENTS

| 7,429,646 B1 * | 9/2008 | Ni et al. .................. 530/388.22 |
| 2002/0102258 A1 * | 8/2002 | Harrop et al. ............. 424/143.1 |
| 2004/0191257 A1 * | 9/2004 | Spear et al. ................ 424/145.1 |
| 2009/0311280 A1 * | 12/2009 | Cheung et al. ............. 424/185.1 |
| 2011/0230647 A1 * | 9/2011 | Murphy et al. ........... 530/387.9 |

FOREIGN PATENT DOCUMENTS

| EP | 1336619 A | 8/2003 |
| WO | 2006/063067 A | 6/2006 |

OTHER PUBLICATIONS

Harrop J et al: "Antibodies to TR2 (herpesvirus entry mediator), a new member of the TNF receptor superfamily, block T cell proliferation, expression of activation markers, and production of cytokines", Journal of Immunology, American Association of Immunologists, US, vol. 161, No. 4, Aug. 15, 1998, pp. 1786-1794.

Tolba Khaled A etal: "HSV amplicon-mediated delivery of LIGHT enhances the antigen-presenting capacity of chronic lymphocytic leukemia." Molecular Therapy : The Journal of the American Society of Gene Therapy Oct. 2002, vol. 6, No. 4, Oct. 2002, pp. 455-463.

Hehlgans T et al: "Recombinant, soluble LIGHT (HVEM ligand) induces increased IL-8 secretion and growth arrest in A375 melanoma cells." Journal of Interferon &Cytokine Research: The Official Journal of the International Society for Interferon and Cytokine Research May 2001, vol. 21, No. 5, May 2001, pp. 333-338.

Kosuge Hisanoriet AL: "Attenuation of graft arterial disease by manipulation of the LIGHT pathway." Arteriosclerosis, Thrombosis, and Vascular Biology Aug. 2004, vol. 24, No. 8, Aug. 2004, pp. 1409-1415.

Costello Regis T et al: "New approaches in the immunotherapy of haematological malignancies." European Journal of Haematology May 2003, vol. 70, No. 5, May 2003, pp. 333-345.

International Search Report in Corresponding Application PCT/EP2008/056756 dated May 6, 2009.

* cited by examiner

*Primary Examiner* — Ilia Ouspenski
(74) *Attorney, Agent, or Firm* — Young & Thompson

(57) ABSTRACT

The present invention relates to ligands of HVEM for the treatment of hematologic malignancies, in particular Chronic lymphocytic leukaemia, and for the treatment of autoimmune diseases.

2 Claims, 13 Drawing Sheets

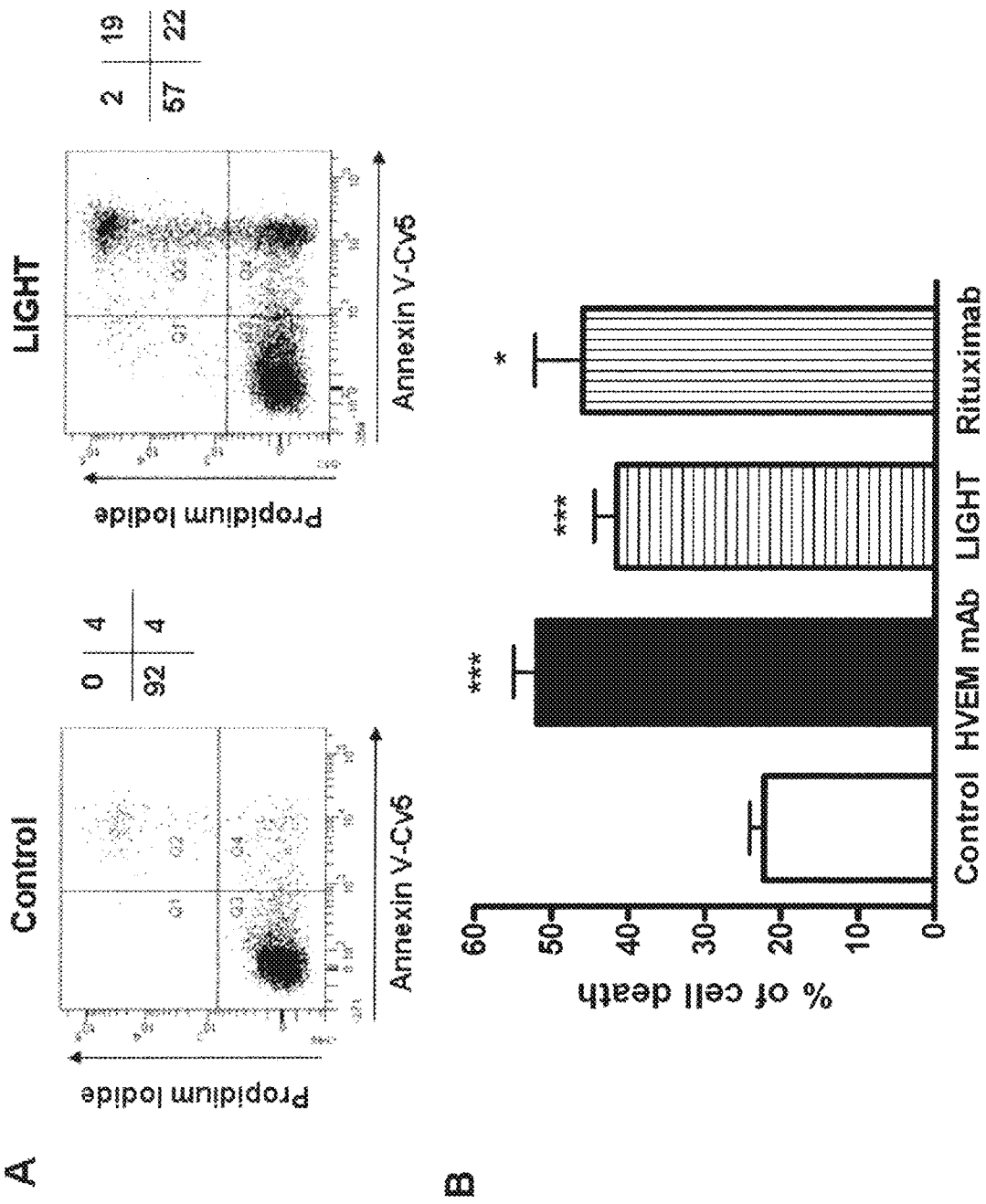

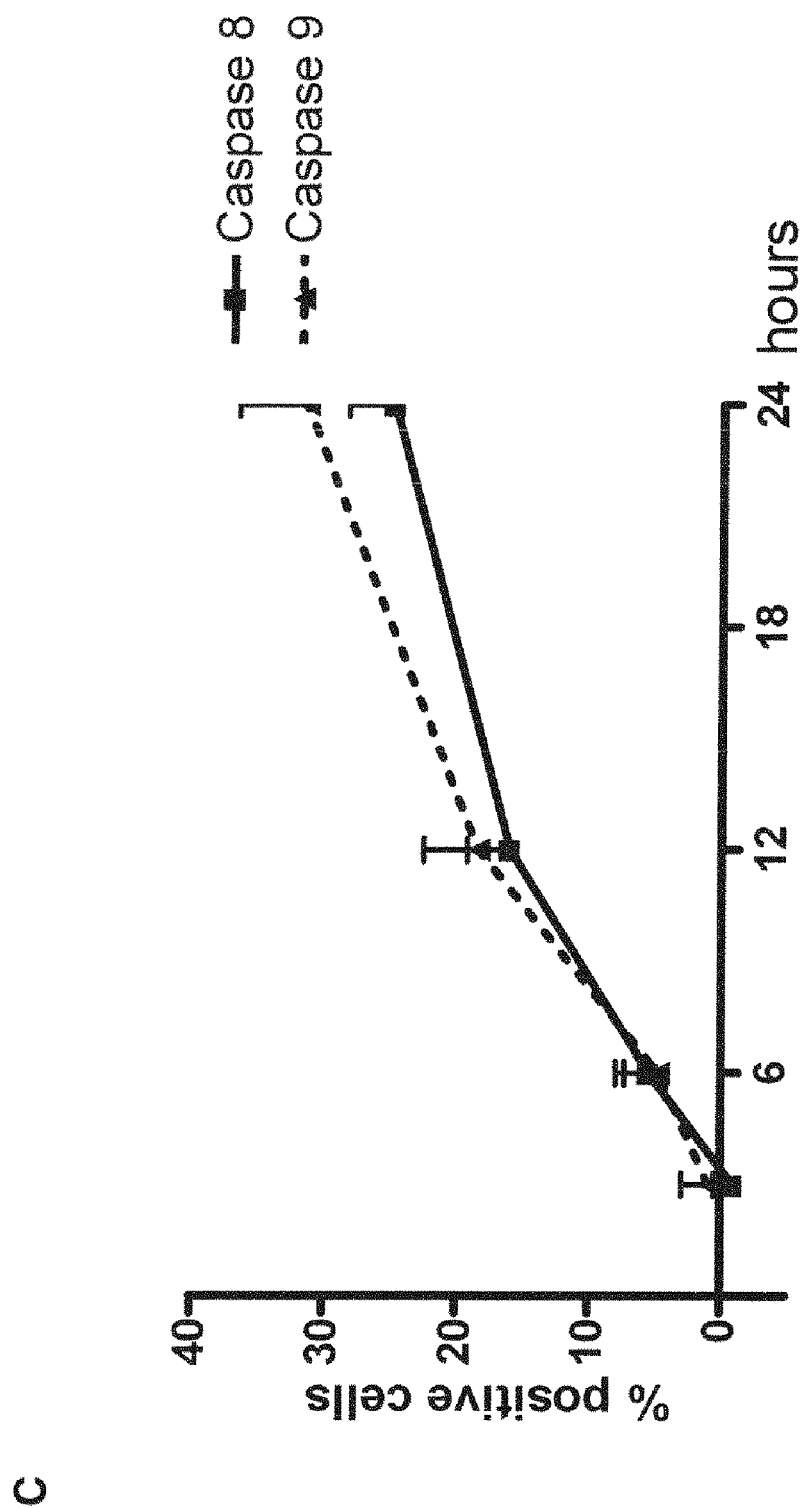

LIGANDS OF HVEM FOR TREATING HEMATOLOGIC MALIGNANCIES

FIELD OF THE INVENTION

Figure 1:
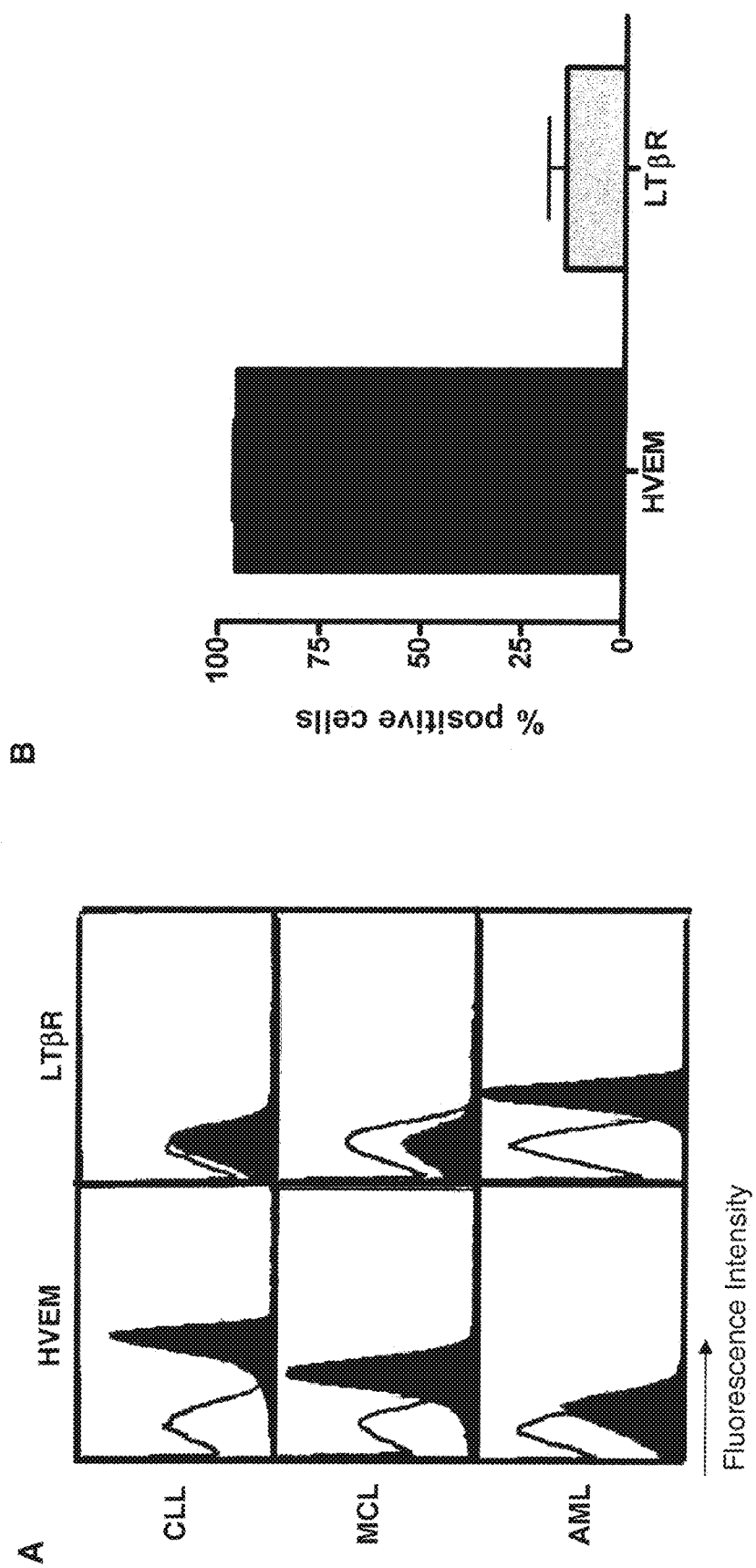

The present invention relates to ligands of HVEM for the treatment of hematologic malignancies, in particular Chronic lymphocytic leukemia (CLL), and for the treatment of autoimmune diseases.

BACKGROUND OF THE INVENTION

Cells of the Immune System

The cells of the immune system originate in the bone marrow, where many of them also mature. They then migrate to patrol the tissues, circulating in blood and in a specialized system of vessels called the lymphatic system.

All the cellular elements of blood including the red blood cells, platelets, and white blood cells of the immune system derive ultimately from the same progenitor or precursor cells, the hematopoietic stem cells in the bone marrow. As these stem cells can give rise to all of the different types of blood cells, they are often referred to as pluripotent hematopoietic stem cells. Initially, they give rise to stem cells of more limited potential which include: i) erythroblasts which give rise erythrocytes or red blood cells, ii) megakaryocytes which are the precursors of platelets, iii) myeloid progenitors which are precursors of the granulocytes, macrophages and mast cells of the innate immune system, and iv) the common lymphoid progenitors which give rise to lymphocytes which are the main components of the adaptive immune systems.

There are two main types of lymphocytes: B lymphocytes or B cells, which when activated differentiate into plasma cells, and T lymphocytes or T cells, of which there are two main classes. Within the T cells, one class differentiate into cytotoxic T cells which kill virally infected cells, whereas the second class differentiate into helper T cells. Helper T cells provide help to the adaptive immune system by activating other lymphocytes such as B cells, and interact with the innate immune system by activating some of the myeloid lineage cells. Although all lymphocytes originate within the bone marrow, which is a primary or central lymphoid organ in humans, only B lymphocytes mature there. T lymphocytes migrate to the thymus, the other central lymphoid organ in humans, to undergo maturation.

Both B and T cells express on their surface, specialized receptors that allow them to recognize antigens. Although collectively these receptors are highly diverse in their antigen specificity, each fully differentiated lymphocyte, and all its progeny, is designed to express receptors that recognize only one antigen. Collectively, the receptors on all the lymphocytes are capable of recognizing a very large repertoire of antigens. The B-cell antigen receptor (BCR) is a membrane-bound form of the antibody that will be secreted when the cells are activated. The T cell antigen receptor (TCR), although related to BCR because of their common structural immunoglobulin roots, is quite distinct from BCR in its antigen binding region, and in the way it interacts with the antigen. A third class of lymphoid cells, called natural killer cells or NK cells, lack antigen-specific receptors and so form part of the innate immune system.

Mature antigen-responsive B lymphocytes develop in the bone marrow prior to their encounter with antigen. The maturation process goes through an orderly series of differentiation stages from the common lymphoid progenitors through the pro-B, pre-B, transitional or immature B, to mature B lymphocytes. Following their encounter with antigen, B cells undergo antigen-induced proliferation and differentiation whose hallmark is the re-arrangement of the immunoglobulin gene locus and expansion of B cell clones. This process ultimately results in the progeny of the B cells secreting antibodies of different heavy and light chain isotypes, or becoming memory cells.

Hematologic Malignancies

With respect to pathological conditions which involve the immune system, the diversity in the lineages and differentiation stages of hematopoietic cells results in a large number of distinct and heterogeneous tumors generally referred to as hematologic malignancies. Thus, hematologic malignancies or hematologic neoplasia affect cells and tissues of the immune and hematopoietic system, including blood, bone marrow and lymph nodes. Hematologic malignancies include both leukemias and lymphomas.

The term leukemia has generally been used to define hematologic malignancies of the blood or bone marrow characterized by abnormal proliferation of leukocytes. The principal subtypes of leukemia are identified on the basis of malignancy involving lymphoid (e.g. T or B lymphocytic lineage) or myeloid (e.g. granulocytic, erythroid or megakaryocytic lineage) cells, and whether the disease is acute or chronic in onset [Freireich, E. J. et al., 1991].

The term lymphoma covers a heterogeneous group of neoplasms of lymphoid tissue. Lymphomas are broadly categorized under Hodgkin lymphoma, and T-cell (T-NHL) and B-cell (B-NHL) non-Hodgkin lymphomas. A World Health Organization (WHO) classification has recently been published (discussed later in this application), and diagnostic guidelines have been established based on this classification [Jaffe, E. S. et al., 2004 (see Table 3 and 4 hereinafter)].

Chronic Lymphocytic Leukemia (CLL) is a form of lymphocytic leukemia characterized by slow but progressive accumulation of lymphocytes in the bone marrow and blood. Depending on the stage of the disease, lymph node and spleen enlargement occur commonly. Although CLL may be of T cell or B cell origin, over 85% of the cases are of B-cell origin. Current understanding suggests that CLL is a heterogeneous disease originating from B lymphocytes that differ in their activation and maturation states and cellular subgroup (see [Kuppers, R., 2005]). The disease may result both from decreased apoptosis as well as increased proliferation of the leukemic B cells. CLL cells are usually clonal in origin, and express the following cell surface markers: CD19, CD20, CD21, and CD24. In addition, they express CD5 which is more typically found on T cells (see [Chiorazzi, N, and al., 2005]).

CLL is considered a subgroup of "non-Hodgkin's lymphoma" (NHL) and together with the closely related disease "small lymphocytic lymphoma" (SLL) which presents primarily in the lymph nodes, corresponds to around 20% of all NHL cases. CLL is the most common leukemia in adults in the US and most of Western Europe. The National Cancer Institute (NCI) estimate for the incidence of CLL is about 10.000 new cases in the US per year. Clinical manifestations of CLL occur predominantly after the age of 55. The incidence rate for men is higher than for women, with men almost twice as likely to acquire the disease as women.

CLL represents an unmet medical need as there are limited options for treatment

The most common treatments for NHL are chemotherapy, in particular a combination regimen called CHOP (for Cytoxan, Hydroxyrubicin [Adriamycin], Oncovin [Vincristine], Prednisone), and radiation therapy. In some cases, surgery and bone marrow transplantation have also been used. More recently, there has been an increase in the use of biopharmaceutical agents, especially monoclonal antibodies, such as rituximab and alemtuzumab. Other combination approaches include the use of biopharmaceuticals such as rituximab with chemotherapy. Although these treatments have significantly improved the management of B-lymphoid malignancies, among their deficiencies include non-responsiveness of many patients to these regimens (some patients become refractory to some or all these approaches), and the side effects and complications which result from the use of these treatments. Among the most common side effects of chemotherapy are nausea and vomiting (which is generally managed with the use of antiemetics), alopecia (which is generally reversed over time after completion of treatment), and leukopenia, especially neutropenia. Neutropenia generally develops in the second week. During this period, many clinicians recommend prophylactic use of ciprofloxacin. If a fever develops in the neutropenic period, urgent medical assessment is required for neutropenic sepsis, as infections in patients with low neutrophil counts may progress rapidly. With respect to rituximab, first infusion reaction, lymphopenia, infectious complications such as viral reactivation including Hepatitis B and Progressive Multifocal Leukoencephalopathy (PML), mucocutaneous reactions, and renal complications have been reported. In the case of alemtuzumab, serious hematologic toxicities can occur, including pancytopenia, bone marrow hypoplasia, autoimmune idiopathic thrombocytopenia, and autoimmune hemolytic anemia. In some cases, these toxicities can accelerate morbidity and mortality rates.

Autoimmune Diseases

The immune system has control mechanisms which prevent it from attacking self tissue. When these mechanisms do not function properly or when they break down, they can result in the development of autoimmunity or autoimmune diseases. Autoimmunity represents a broad spectrum of diseases from the organ specific to the non-organ specific. At one end of the spectrum, Hashimoto's thyroditis typifies the highly organ specific diseases where the destructive lesion is directed at one organ only. At the other end of the spectrum, lupus erythomatosus (SLE) represents the non-organ specific diseases where the tissues involved are widespread throughout the body. With improvements in our understanding of immunobiology, and advances in molecular and diagnostic tools, it is becoming progressively evident that most organ or tissue systems can be subject to the autodestructive potential of autoimmune diseases as is shown in the following list. Thus among the autoimmune diseases are included: Addison's disease, ankylosing spondylitis, aplastic anemia, autoimmune hemolytic anemia, autoimmune hepatitis, coeliac disease, Crohn's disease, dermatomyositis, Goodpasture's syndrome, Graves' disease, Guillain-Barré syndrome, Hashimoto's disease, idiopathic leucopenia, idiopathic thrombocytopenic purpura, insulin dependent diabetes mellitus (Type 1 diabetes), male infertility, mixed connective tissue disease, multiple sclerosis (MS), myasthenia gravis, pemphigoid, pemphigus vulgaris, pernicious anemia, phacogenic uveitis, primary biliary cirrhosis, primary myxoedema, Reiter's syndrome, rheumatoid arthritis (RA), scleroderma, Sjögren's syndrome, stiff man syndrome, systemic lupus erythematosus (SLE), thyrotoxicosis, ulceritive colitis, and Wegener's granulomatosis.

The etiology of autoimmune diseases is not completely understood. In some instances, mechanisms of molecular mimicry have been proposed whereby a productive anti-bacterial or anti-viral response may inadvertently result in the development of immunological responses to self tissue. In addition, inherited or genetic predispositions are known to contribute to the development of many of these diseases.

Both lymphoid and myeloid lineage cells have been implicated in the development of autoimmune diseases. Autoreactive T and B lymphocytes determine the principal clinicopathologic features of each disease and the tissue involved. T lymphocytes may attack self tissue directly whereas B cells secrete autoreactive antibodies. In SLE, copious of self reactive antibodies including antibodies to double-stranded DNA are produced which are believed to cause or exacerbate kidney damage. Myeloid lineage cells such are macrophages help to maintain, amplify and extend the immune attack against self tissue by providing cytokine and chemokine responses such as TNF-α and IL-8, as well as by serving as effector cells for the autodestructive processes. A role for TNF-α has been clearly established for RA and Crohn's disease which are now known to respond to anti-TNF-α therapies. In the case of RA, myeloid lineage cells are believed to differentiate to osteoclasts thus causing bone damage and destruction of synovial linings with the inflamed joints. RA patients have also been shown to respond to treatments directed against B cells, such as anti-CD20 antibody therapy.

SUMMARY OF THE INVENTION

The invention relates to a ligand of HVEM for therapeutic use, wherein said ligand of HVEM is selected from the group consisting of LIGHT, a fragment of LIGHT which induces apoptosis in chronic lymphocytic leukemia B cells, an anti-HVEM antibody and a fragment thereof which binds to HVEM.

In particular the invention relates to a ligand of HVEM for the treatment of hematologic malignancies or autoimmune diseases.

The invention also relates to a method of treatment of hematologic malignancies or autoimmune diseases which comprises administering to a subject in need thereof a therapeutically effective amount of a ligand of HVEM.

Definitions

As used herein, references to specific proteins (e.g., antibodies or LIGHT) can include a polypeptide having a native amino acid sequence, as well as variants and modified forms regardless of their origin or mode of preparation. A protein that has a native amino acid sequence is a protein having the same amino acid sequence as obtained from nature (e.g., a naturally occurring LIGHT). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. A native sequence protein includes proteins following post-translational modifications such as glycosylation, or phosphorylation, or other modifications of some amino acid residues.

The term "HVEM", as used herein, is intended to encompass all synonyms including, but not limited to, "Herpes Virus Entry Mediator", "HVEA", "Herpes Virus Entry Mediator A", "TNFRSF14", "Tumor Necrosis Factor Receptor Superfamily Member 14", "TNR14", "LIGHTR", "LIGHT receptor", "TR2", "TNF Receptor-like", "ATAR", "Another TRAF-Associated Receptor". TNFRSF14 is the HUGO (Human Genome Organization) Gene Nomenclature Committee (HGNC) approved symbol. The UniProtKB/Swiss-Prot "Primary Accession Number" for HVEM is Q92956. The "Secondary Accession Numbers" are Q8WXR1, Q96J31 and Q9UM65.

By "ligand" is meant a natural or synthetic compound which binds to a receptor molecule to form a receptor-ligand complex.

So far, four ligands have been identified which bind to HVEM. Two of these ligands, LIGHT and LTα, are member of the TNF family of molecules (Morel, Y. et al., 2000; Mauri, D. N. et al., 1998 and Harrop, J. A. et al., 1998). Structurally, members of the TNF family are generally expressed as single-pass type 2 transmembrane, homotrimer or heterotrimer, glycoproteins. Following their expression as transmembrane proteins, they are cleaved by proteolytic action to produce a soluble form of the ligand. The third ligand for HVEM, BTLA, a type 1 transmembrane glycoprotein, is a member of the immunoglobulin (Ig) superfamily of molecules and is closely related to CD28 (Gonzalez, L. C. et al., 2005). The fourth ligand, glycoprotein D (gD), is a structural component of the herpes simplex virus (HSV) envelope, and is essential for HSV entry into host cells (Montgomery, R. I. et al., 1996; Hsu, H. et al., 1997; Kwon, B. S. et al., 1997; Tan, K. B. et al., 1997; Marsters, S. A. et al., 1997; Wallach, D. et al., 1999; Collette, Y. et al., 2003; Harrop, J. A. et al., 1998; Gonzalez, L. C. et al., 2005 and Whitbeck, J. C. et al., 1997)

Binding studies (Gonzalez, L. C. et al., 2005 and Sedy, J. R. et al., 2005) which were later supported by crystallography (Compaan, D. M. et al., 2005) indicate that BTLA interacts with the most membrane-distal CRD region of HVEM. The membrane-distal CRD1 region of HVEM has also been implicated in the interactions with HSV-gD, with additional contributions from CRD2 (Compaan, D. M. et al., 2005 and Carfi, A. et al., 2001). Despite the sequence and structural dissimilarities between BTLA and HSV-gD, the crystal structure studies also show that their binding sites on HVEM cover largely overlapping surfaces (Compaan, D. M. et al., 2005 and Carfi, A. et al., 2001)

The term "LIGHT", as used herein, is intended to encompass all synonyms including, but not limited to, "lymphotoxins, inducible, competes with herpes simplex virus (HSV) glycoprotein D for HVEM, expressed by T cells", "TNFSF14", "Tumor Necrosis Factor Ligand Superfamily Member 14", "TNF14_HUMAN", "HVEM-L", "HVEML", "HVEM-Ligand", "Herpes Virus Entry Mediator Ligand", "Herpesvirus entry mediator-ligand", "TL4", "TNF-like 4", "TN14", "LTγ" and "CD258". TNFSF14 is the HGNC approved symbol. CD258 is the cluster designation assignment of the HLDA (Human Leukocyte Differentiation Antigens) Workshop. The UniProtKB/Swiss-Prot "Primary Accession Number" for LIGHT is O43557. The "Secondary Accession Numbers" are O75476, Q8WVF8 and Q96LD2.

In natural antibodies, the two heavy chains are linked to each other by disulfide bonds and each heavy chain is linked to a light chain by a disulfide bond. There are two types of light chains, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin consisting of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs. The term "antibody" is further intended to encompass antibodies, digestion fragments, specified portions and variants thereof, including antibody mimetics or portions of antibodies that mimic the structure and/or function of an antibody or specified fragment or portion thereof, including single chain antibodies and fragments thereof. Functional fragments include antigen-binding fragments that bind to a mammalian HVEM.

As used herein, the term "human antibody" refers to an antibody in which a substantial portion of the antibody molecule resembles, in amino acid sequence or structure, that of an antibody derived from human origin. The term "humanized antibody" refers to an antibody which has been modified by genetic engineering or by other means to be similar in structure or amino acid sequence to naturally occurring human antibodies. A "human antibody" or a "humanized antibody" may be considered more suitable in instances where it is desirable to reduce the immunogenicity of the antibody for administration to humans for therapeutic, prophylactic or diagnostic purposes.

A "monoclonal antibody" or "mAb" in its various names refers to a population of antibody molecules that contains only one species of antibody combining site capable of immunoreacting with a particular epitope. A monoclonal antibody thus typically displays a single binding affinity for any epitope with which it immunoreacts. Monoclonal antibody may also define an antibody molecule which has a plurality of antibody combining sites, each immunospecific for a different epitope. For example, a bispecific antibody would have two antigen binding sites, each recognizing a different interacting molecule, or a different epitope. As used herein, the terms "antibody fragment", "antibody portion", "antibody variant" and the like include any protein or polypeptide containing molecule that comprises at least a portion of an immunoglobulin molecule such as to permit specific interaction between said molecule and an antigen (e.g. HVEM). The portion of an immunoglobulin molecule may include, but is not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of a ligand or counter-receptor (e.g. LIGHT, BTLA or HSV-gD) which can be incorporated into an antibody of the present invention to permit interaction with the antigen (e.g. HVEM).

The term "hybridoma" denotes a cell, which is obtained by subjecting a B cell, prepared by immunizing a non-human mammal with an antigen, to cell fusion with a myeloma cell derived from a mouse or the like which produces a desired monoclonal antibody having an antigen specificity.

As used herein, the term "subject" denotes a mammal, such as a rodent, a feline, a canine, and a primate. Preferably a subject according to the invention is a human.

DETAILED DESCRIPTION OF THE INVENTION

Therapeutic Methods and Uses

A first object of the invention relates to a ligand of HVEM for therapeutic use, wherein said ligand of HVEM is selected from the group consisting of LIGHT, a fragment of LIGHT which induces apoptosis in chronic lymphocytic leukemia B cells, an anti-HVEM antibody and a fragment thereof which binds to HVEM.

Typically said ligand of HVEM may be used in combination with radiotherapy and hormone therapy.

Typically said ligand of HVEM may also be used in combination with a one or more agents selected from the group consisting of an anticancer agent, an antiemetic agent, an hematopoietic colony stimulating factor, an analgesic agent and an anxiolytic agent.

In a preferred embodiment, the invention relates to a ligand of HVEM for the treatment of hematologic malignancies or autoimmune diseases.

The invention also relates to the use of a ligand of HVEM for the manufacture of a medicament for the treatment of hematologic malignancies or autoimmune diseases, wherein said ligand of HVEM is selected from the group consisting of LIGHT, a fragment thereof, which induces apoptosis in chronic lymphocytic leukemia B cells, an anti-HVEM antibody and a fragment thereof which binds to HVEM.

In one embodiment, hematologic malignancies include but are not limited to lymphoid cell neoplasms such as chronic lymphocytic leukaemia (CLL), non-Hodgkin lymphoma (NHL), small lymphocytic lymphoma (SLL), and mantle cell lymphoma (MCL). More specifically, non-Hodgkin lymphoma (NHL) include B and T non-Hodgkin lymphoma. Furthermore, cell lymphoid neoplasms include B, NK and T cell lymphoid neoplasms.

In one embodiment, autoimmune diseases include but are not limited to Addison's disease, ankylosing spondylitis, aplastic anemia, autoimmune hemolytic anemia, autoimmune hepatitis, coeliac disease, Crohn's disease, dermatomyositis, Goodpasture's syndrome, Graves' disease, Guillain-Barré syndrome, Hashimoto's disease, idiopathic leucopenia, idiopathic thrombocytopenic purpura, insulin dependent diabetes mellitus (Type 1 diabetes), male infertility, mixed connective tissue disease, multiple sclerosis (MS), myasthenia gravis, pemphigoid, pemphigus vulgaris, pernicious anemia, phacogenic uveitis, primary biliary cirrhosis, primary myxoedema, Reiter's syndrome, rheumatoid arthritis (RA), scleroderma, Sjögren's syndrome, stiff man syndrome, systemic lupus erythematosus (SLE), thyrotoxicosis, ulceritive colitis, and Wegener's granulomatosis.

In a preferred embodiment, said ligand of HVEM is LIGHT or a fragment thereof, which induces apoptosis in chronic lymphocytic leukemia B cells.

Specifically, said ligand may consist of a polypeptide, comprising a sequence with at least 90% identity with the sequence whose accession number is Q92956 and which induces apoptosis in chronic lymphocytic leukemia B cells.

In another preferred embodiment, the ligand of the invention is LIGHT that may be used in a soluble form.

Polypeptides of the invention may be produced by any technique known per se in the art, such as, without limitation, any chemical, biological, genetic or enzymatic technique, either alone or in combination(s).

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques. Polypeptides of the invention can be used in an isolated (e.g., purified) form or contained in a vector, such as a membrane or lipid vesicle (e.g. a liposome).

In another preferred embodiment, said ligand of HVEM is an anti-HVEM antibody or a fragment thereof which binds to HVEM.

Said ligand may induce death and/or elimination of malignant lymphocytes expressing HVEM by mechanisms such as induction of apoptosis, antibody-dependent cellular cytotoxicity, complement-mediated cytotoxicity, or recruitment and/or activation of immune effector cells through the production of cytokines or chemokines.

In a preferred embodiment, said ligand induces apoptosis in malignant lymphocytes expressing HVEM, in chronic lymphocytic leukemia B cells in particular.

Malignant lymphocytes expressing HVEM may be obtained from patients suffering from acute leukemia, chronic lymphocytic leukemia, plasma cell leukemia, multiple myeloma, B cell lymphoma or T cell lymphoma.

In an embodiment of the invention said anti-HVEM antibody or said fragment thereof is an antibody or a fragment thereof, which does not inhibit the binding of BTLA to HVEM.

In an alternative embodiment of the invention said anti-HVEM antibody or said fragment thereof is an antibody or a fragment thereof, which inhibits the binding of BTLA to HVEM and which does not bind to a sequence of 30 amino acids comprising or consisting of human HVEM sequence CPKCSPGYRVKEACGELTGTVCEPC (SEQ ID NO:1).

In a preferred embodiment said anti-HVEM antibody or said fragment is an antibody or a fragment thereof which recognizes an epitope selected from the group consisting of groups I, II, III, IV, V or VI. In another preferred embodiment said anti-HVEM antibody or said fragment is an antibody or a fragment thereof which recognizes an epitope selected from the group consisting of groups II, IV, or V.

The epitopes recognized by the HVEM mAbs are characterized by the following features:
i) The ability of the mAbs to inhibit the binding of LIGHT, HSV-gD and/or BTLA to HVEM.
ii) Mutagenesis experiments whereby the mAbs were tested for their ability to bind to mutants of HVEM.

The HVEM mutants used include:
i) Two deletion mutants
   a. CRD1 domain deletion and
   b. Deletion of amino acids 129-133 within the CRD3 domain (del129-133)
ii) An alanine substitution mutant with substitution of residues 131-133 (mut131-133)

The above set of experiments defines 6 distinct groups of mAbs and thus 6 epitopes:
1. Group I mAbs correspond to those which do not bind to the CRD1 but are affected by del129-133 deletion mutants and only block the binding of HVEM to LIGHT.
2. Group II mAbs correspond to those which bind to the CRD1 deletion but not to the del129-133 deletion, or the mut131-133 mutant.
3. Group III mAbs correspond to those which do not bind to the CRD1 deletion mutant and are not affected by the del129-133 deletion, and do not inhibit the binding of the three HVEM ligands.
4. Group IV mAbs correspond to those which are not affected by the CRD1 but are affected by del129-133 deletion mutants, and do not inhibit the binding of the three HVEM ligands.
5. Group V mAbs correspond to those which bind to the CRD1 deletion but not to the del129-133 deletion, are not affected by the mut131-133 mutant, and are not able to block HVEM binding to the three ligands.
6. Group VI mAbs correspond to those which bind to the CRD1 deletion but are affected in part by the del129-133 deletion, or by the mut131-133 mutant, and are able to block HVEM binding to all ligands.

In a preferred embodiment said anti-HVEM antibody is a monoclonal antibody obtainable from a hybridoma deposited in accordance with the Budapest Treaty, on Apr. 26, 2007 at the COLLECTION NATIONALE DE CULTURES DE MICROORGANISMES (CNCM) selected from the group consisting of CNCM I-3752, CNCM I-3753 and CNCM I-3754.

In a further embodiment, the invention relates to a hybridoma cell line suitable for obtaining anti-HVEM monoclonal antibodies, which induce death and/or elimination of malignant lymphocytes by mechanisms such as induction of apoptosis, antibody-dependent cellular cytotoxicity, complement-mediated cytotoxicity, or recruitment and/or activation of immune effector cells through the production of cytokines or chemokines.

In a preferred embodiment, the invention relates to a hybridoma cell line suitable for obtaining anti-HVEM monoclonal antibodies, which induce apoptosis in malignant lymphocytes expressing HVEM, in chronic lymphocytic leukemia B cells in particular.

In a preferred embodiment, the invention relates to a hybridoma cell line suitable for obtaining anti-HVEM monoclonal antibodies, which recognize an epitope selected from the group consisting of groups I, II, III, IV, V or VI.

In a preferred embodiment said hybridoma cell line is selected from the group consisting of CNCM I-3752, CNCM I-3753 and CNCM I-3754.

Whereas polyclonal antibodies may be used, monoclonal antibodies are preferred. Antibodies capable of specific binding to HVEM may be derived from a number of species including, but not limited to, rodent (mouse, rat, rabbit, guinea pig, hamster, and the like), porcine, bovine, equine or primate and the like. Antibodies from primate (monkey, baboon, chimpanzee, etc.) origin have the highest degree of similarity to human sequences and are therefore expected to be less immunogenic. Antibodies derived from various species can be "humanized" by modifying the amino acid sequences of the antibodies while retaining their ability to bind the desired antigen. Antibodies may also be derived from transgenic animals, including mice, which have been genetically modified with the human immunoglobulin locus to express human antibodies. Procedures for raising "polyclonal antibodies" are well known in the art. For example, polyclonal antibodies can be obtained from serum of an animal immunized against HVEM, which may be produced by genetic engineering for example according to standard methods well-known by one skilled in the art. Typically, such antibodies can be raised by administering HVEM protein subcutaneously to New Zealand white rabbits which have first been bled to obtain pre-immune serum. The antigens can be injected at a total volume of 100 μl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times at six weeks' interval. A sample of serum is then collected 10 days after each boost. Polyclonal antibodies are then recovered from the serum by affinity chromatography using the corresponding antigen to capture the antibody. This and other procedures for raising polyclonal antibodies are disclosed by (Harlow et al., 1988), which is hereby incorporated in the references.

Although historically monoclonal antibodies were produced by immortalization of a clonally pure immunoglobulin secreting cell line, a monoclonally pure population of antibody molecules can also be prepared by the methods of the present invention. Laboratory methods for preparing monoclonal antibodies are well known in the art (see, for example, Harlow et al., 1988). Monoclonal antibodies (mAbs) may be prepared by immunizing a mammal such as mouse, rat, primate and the like, with purified HVEM protein. The antibody-producing cells from the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in (Kohler and Milstein, 1975). Alternatively, the immunoglobulin genes may be isolated and used to prepare a library for screening for reactive specifically reactive antibodies. Many such techniques including recombinant phage and other expression libraries are known to one skilled in the art. While mAbs can be produced by hybridoma culture the invention is not to be so limited. Also contemplated is the use of mAbs produced by cloning and transferring the nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al.

In a particular embodiment, mAbs recognizing HVEM may be generated by immunization of Balb-c mice with the respective recombinant human Fc-IgG1 fusion proteins. Spleen cells were fused with X-63 myeloma cells and cloned according to already described procedures (Olive D, 1986).

Hybridoma supernatants were then screened by staining of transfected cells and for lack of reactivity with untransfected cells.

Antibody generation techniques not involving immunisation are also contemplated such as for example using phage display technology to examine naive libraries (from non-immunised animals); see (Barbas et al., 1992, and Waterhouse et al. (1993).

Antibodies of the invention are suitably separated from the culture medium by conventional immunoglobulin purification procedures such as, for example, affinity, ion exchange and/or size exclusion chromatography, and the like In a particular embodiment, the antibody of the invention may be a human chimeric antibody. Said human chimeric antibody of the present invention can be produced by obtaining nucleic sequences encoding VL and VH domains, constructing a human chimeric antibody expression vector by inserting them into an expression vector for animal cell having genes encoding human antibody CH and human antibody CL, and expressing the expression vector by introducing it into an animal cell. The CH domain of a human chimeric antibody may be any region which belongs to human immunoglobulin, but those of IgG class are suitable and any one of subclasses belonging to IgG class, such as IgG1, IgG2, IgG3 and IgG4, can also be used. Also, the CL of a human chimeric antibody may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

In another particular embodiment, said antibody may be a humanized antibody. Said humanized antibody may be produced by obtaining nucleic acid sequences encoding for CDRs domain by inserting them into an expression vector for animal cell having genes encoding a heavy chain constant region identical to that of a human antibody; and a light chain constant region identical to that of a human antibody, and expressing the expression vector by introducing it into an animal cell.

The humanized antibody expression vector may be either of a type in which a gene encoding an antibody heavy chain and a gene encoding an antibody light chain exist on separate vectors or of a type in which both genes exist on the same vector (tandem type). In respect of easiness of construction of a humanized antibody expression vector, easiness of introduction into animal cells, and balance between the expression levels of antibody H and L chains in animal cells, a tandem type of the humanized antibody expression vector is more preferable (Shitara K et al. 1994). Examples of the tandem type humanized antibody expression vector include pKANTEX93 (WO 97/10354), pEE18 and the like. Methods for producing humanized antibodies based on conventional recombinant DNA and gene transfection techniques are well known in the art (See, e.g. Riechmann L et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576). For example, antibody fragments capable of binding to HVEM or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments may be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. The various portions of antibodies can be joined together chemically by conventional techniques, or can be prepared as a contiguous protein using genetic engineering techniques.

Said Fab fragment of the present invention can be obtained by treating an antibody which specifically reacts with human HVEM with a protease, papaine. Also, the Fab may be produced by inserting DNA encoding Fab of the antibody into a vector for prokaryotic expression system or for eukaryotic expression system, and introducing the vector into a procaryote or eucaryote to express the Fab.

Said F(ab')$_2$ of the present invention may be obtained by treating an antibody which specifically reacts with HVEM with a protease, pepsin. Also, the F(ab')$_2$ can be produced by binding Fab' described below via a thioether bond or a disulfide bond. Said Fab' may be obtained by treating F(ab')$_2$ which specifically reacts with HVEM with a reducing agent, dithiothreitol. Also, the Fab' can be produced by inserting DNA encoding Fab' fragment of the antibody into an expression vector for prokaryote or an expression vector for eukaryote, and introducing the vector into a prokaryote or eukaryote to effect its expression.

Said scFv fragment may be produced by obtaining cDNA encoding the $V_H$ and $V_L$ domains as previously described, constructing DNA encoding scFv, inserting the DNA into an expression vector for prokaryote or an expression vector for eukaryote, and then introducing the expression vector into a prokaryote or eukaryote to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816,567; EP0173494).

In a particular embodiment, monoclonal antibodies of the invention are monovalent, bivalent, multivalent, monospecific, bispecific, or multispecific. In another preferred embodiment, the antibody to HVEM is a binding fragment or a conjugate. For examples antibodies of the invention may be conjugated to a growth inhibitory agent, cytotoxic agent, or a prodrug-activating enzyme.

It may be also desirable to modify the antibody of the invention with respect to effector functions, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC)

(Caron P C. et al. 1992; and Shopes B. 1992) Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non-proteinaceous polymers, e.g. polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

A further object of the invention relates to a method of treating hematologic malignancies and autoimmune diseases comprising administering in a subject in need thereof a therapeutically effective amount of ligand of HVEM as defined above.

In the context of the invention, the term "treating" or "treatment", as used herein, means reversing, alleviating, inhibiting the progress of, or preventing the disorder or condition to which such term applies, or one or more symptoms of such a disorder or condition.

According to the invention, the term "patient" or "patient in need thereof" is intended for a human or non-human mammal affected or likely to be affected by a hematologic malignancy or by an autoimmune disease.

By a "therapeutically effective amount" of the ligand of HVEM according to the invention is meant a sufficient amount of the ligand of HVEM to treat said hematologic malignancy or autoimmune disease, at a reasonable benefit/risk ratio applicable to any medical treatment. It will be understood, however, that the total daily usage of the ligand of HVEM and compositions of the present invention will be decided by the attending physician within the scope of sound medical judgment. The specific therapeutically effective dose level for any particular patient will depend upon a variety of factors including the disorder being treated and the severity of the disorder, activity of the specific ligand of HVEM employed; the specific composition employed, the age, body weight, general health, sex and diet of the patient, the time of administration, route of administration, and rate of excretion of the specific antibody employed, the duration of the treatment; drugs used in combination or coincidental with the specific polypeptide employed, and like factors well known in the medical arts. For example, it is well known within the skill of the art to start doses of the compound at levels lower than those required to achieve the desired therapeutic effect and to gradually increase the dosage until the desired effect is achieved.

Ligands of HVEM according to the invention may be used in combination with any other therapeutic strategy for treating the disorders or conditions as above described (e.g. external radiotherapy, chemotherapy or cytokine therapy).

Pharmaceutical Compositions

A further object of the invention relates to a pharmaceutical composition comprising an effective dose of a ligand of HVEM.

Any therapeutic agent of the invention as above described may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of a ligand of HVEM may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

A ligand of HVEM of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g. tablets or other solids for oral administration; time release capsules; and any other form currently used.

Compositions of the present invention may comprise a further therapeutic active agent. The present invention also relates to a kit comprising a ligand of HVEM as defined above and a further therapeutic active agent.

In one embodiment said therapeutic active agent is an anticancer agent. For example, said anticancer agents include but are not limited to fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxin, hormonal therapies, retinoids, photosensitizers or photodynamic therapies, angiogenesis inhibitors, antimitotic agents, isoprenylation inhibitors, cell cycle inhibitors, actinomycins, bleomycins, anthracyclines, MDR inhibitors and Ca2+ ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Additional anticancer agent may be selected from, but are not limited to, growth or hematopoietic factors such as erythropoietin and thrombopoietin, and growth factor mimetics thereof.

In the present methods for treating cancer the further therapeutic active agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoemanolamine, alizapride, azasetron, benzquinamide, bietanautine, bromopride, buclizine, clebopride, cyclizine, dunenhydrinate, diphenidol, dolasetron, meclizme, methallatal, metopimazine, nabilone, oxypemdyl, pipamazine, scopolamine, sulpiride, tetrahydrocannabinols, thiefhylperazine, thioproperazine and tropisetron. In a preferred embodiment, the anti-emetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the other therapeutic active agent can be an opioid or non-opioid analgesic agent Suitable opioid analgesic agents include, but are not limited to, morphine, heroin, hydromorphone, hydrocodone, oxymorphone, oxycodone, metopon, apomorphine, nomioiphine, etoipbine, buprenorphine, mepeddine, lopermide, anileddine, ethoheptazine, piminidine, betaprodine, diphenoxylate, fentanil, sufentanil, alfentanil, remifentanil, levorphanol, dextromethorphan, phenazodne, pemazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

Screening Methods

Fragments of LIGHT which induce apoptosis in chronic lymphocytic leukemia B cells, anti-HVEM antibodies or fragments thereof which bind to, and induce apoptosis in malignant lymphocytes expressing HVEM, in chronic lymphocytic leukemia B cells in particular may be selected by any screening methods well known in the art.

For example, a method for the in vitro screening of ligands of HVEM which induce apoptosis in malignant lymphocytes expressing HVEM, in chronic lymphocytic leukemia B cells in particular, may comprise the following steps:
  (a) adding fragments of LIGHT, anti-HVEM antibodies, or fragments thereof to malignant lymphocytes expressing HVEM e.g. chronic lymphocytic leukemia B cells;
  (b) selecting the fragments or the antibodies which induce the apoptosis of the cells.

The ability of fragments of LIGHT or anti-HVEM antibodies to induce apoptosis in chronic lymphocytic leukemia B cells can be measured as disclosed in the experimental section, or by any other method known by the man skilled in the art.

The invention will be further illustrated through the following examples, figures and tables.

FIGURES

FIG. 1: Expression of HVEM and LTβR on hematopoietic malignancies (A) Surface expression of HVEM and LTβR on chronic lymphocytic leukemia (CLL), mantle cell lymphoma (MCL) and acute myeloid leukemia (AML) was monitored by flow cytometry. Represented are 2 of 9 CLL patients, 1 of 2 MCL patients and 1 of 2 AML patients. The open histograms represent the fluorescence of the cells stained with isotype-matched controls mAbs of irrelevant specificity. The filled histograms represent staining with specific HVEM-FITC or LTβR-PE conjugated mAbs. (B) The bars represent the mean percentage of positive cells for HVEM and LTβR (after subtraction of the background corresponding to the isotype-matched control) performed on 9 B-CLL patients. The error bars indicate the standard error of the mean (SEM).

Figure 2:
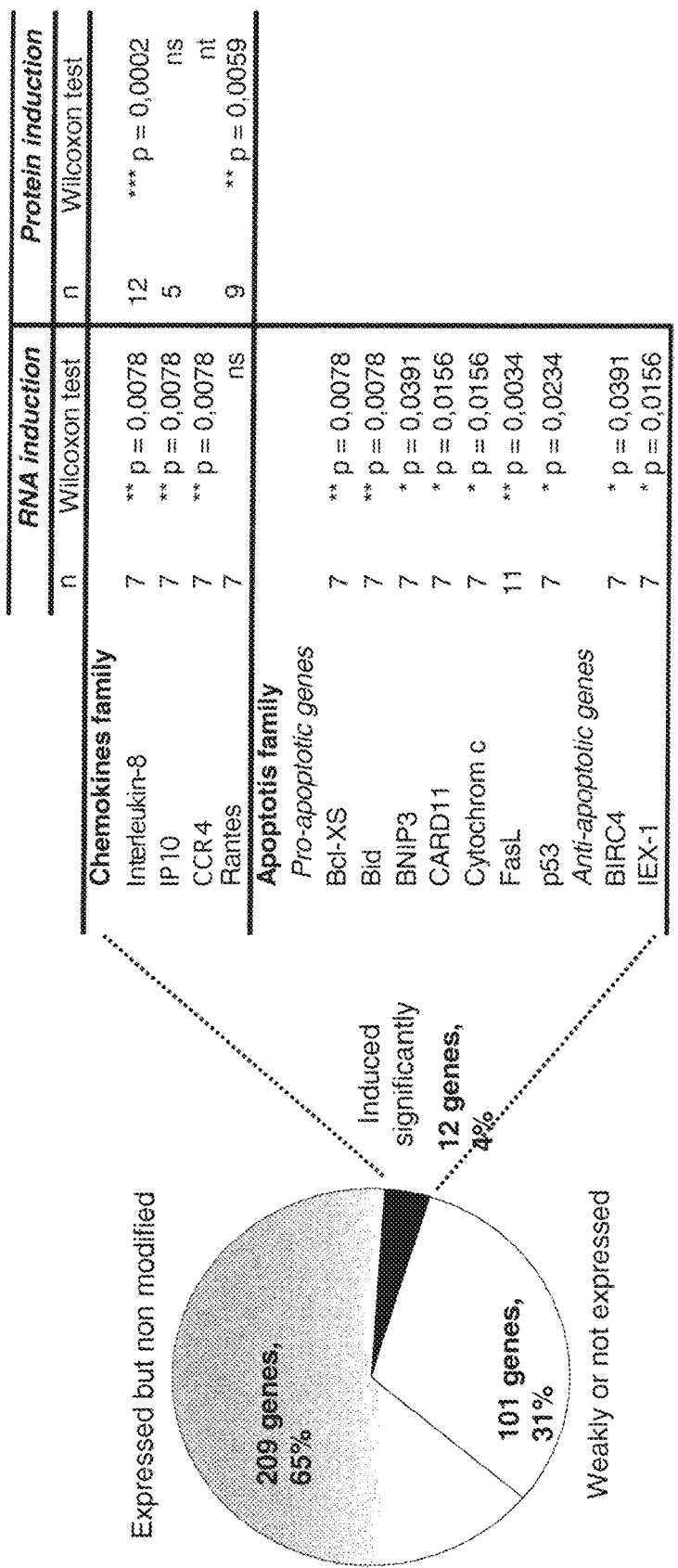

FIG. 2: Genes significantly induced after HVEM stimulation in B-CLL cells among the 322 genes tested by QRT-PCR RNA was quantified by QRT-PCR in B-CLL cells treated or not with anti-HVEM mAb for 24 hours. RNA expression was normalized using β-actin as endogenous control, and ΔCt value was calculated with ΔCt=Ct target−Ct endogenous control. Cytokine release was determined by CBA or Elisa (as described in Material and Methods) in supernatants of B-CLL cells treated or not with anti-HVEM mAb for 24 hours. Significant difference between the HVEM mAb treated and the non treated conditions was tested with the Wilcoxon signed-rank test (one tailed), and p values are presented in this table (n represents number of patients; ns: non significative, nt: not tested).

Figure 3:
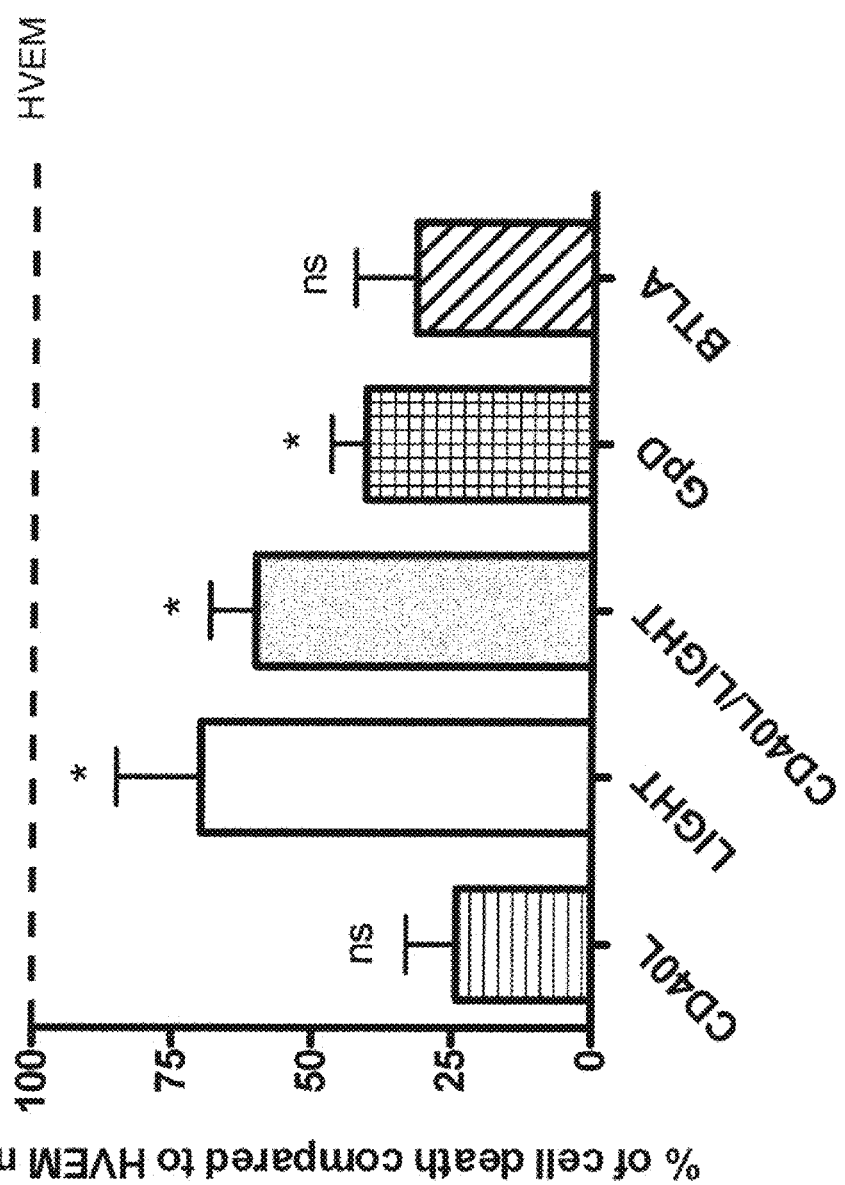

FIG. 3: LIGHT and HVEM mAb induce death of B-CLL cells (A) B-CLL cells were incubated with CD32- (control) or LIGHT-transfected L-cells with a ration of 1 transfectant for 10 leukemic cells. After 24 hours of incubation, cells were analyzed by flow cytometry with Annexin V/PI double staining as described in Material & Methods: dead cells include Annexin $V^+/PI^-$ (early apoptosic) and Annexin $V^+/PI^+$ (late apoptotic/necrotic) cells. The figure shows one representative experiment out of 15 performed. (B) B-CLL cells were incubated with CD32- (control) or LIGHT-transfected L-cells, or treated with 30 μg/ml of the anti-HVEM mAb or 10 μg/ml therapeutic anti-CD20 (Rituximab) mAb, and analyzed by Annexin V/PI staining. The bars depict the mean percentage of dead cells observed ±SEM, with n=25 for HVEM mAb, n=15 for LIGHT-transfected cells, and n=5 for Rituximab. $*p<0.05$; $p<0.01$; $*p<0.001$. (C) Effects of HVEM ligands compared to HVEM mAb stimulation. B-CLL cells were co-cultured with CD32- (control), CD40L-, LIGHT-, CD40L/LIGHT-, GpD, or BTLA-transfected L-cells for 24 hours, and analysed by Annexin V/PI staining. A 100% value to the level of cell death achieved using HVEM mAb was used to compare the levels of B-CLL cells killing by L-cells transfected with HVEM ligands. CD40L-L cells were used as negative control. Apoptosis induced was calculated relative as (percent apoptosis induced by transfected cells divided by percent apoptosis of HVEM mAb×100)±SEM for 6 different patients. $*p<0.05$.

Figure 4:
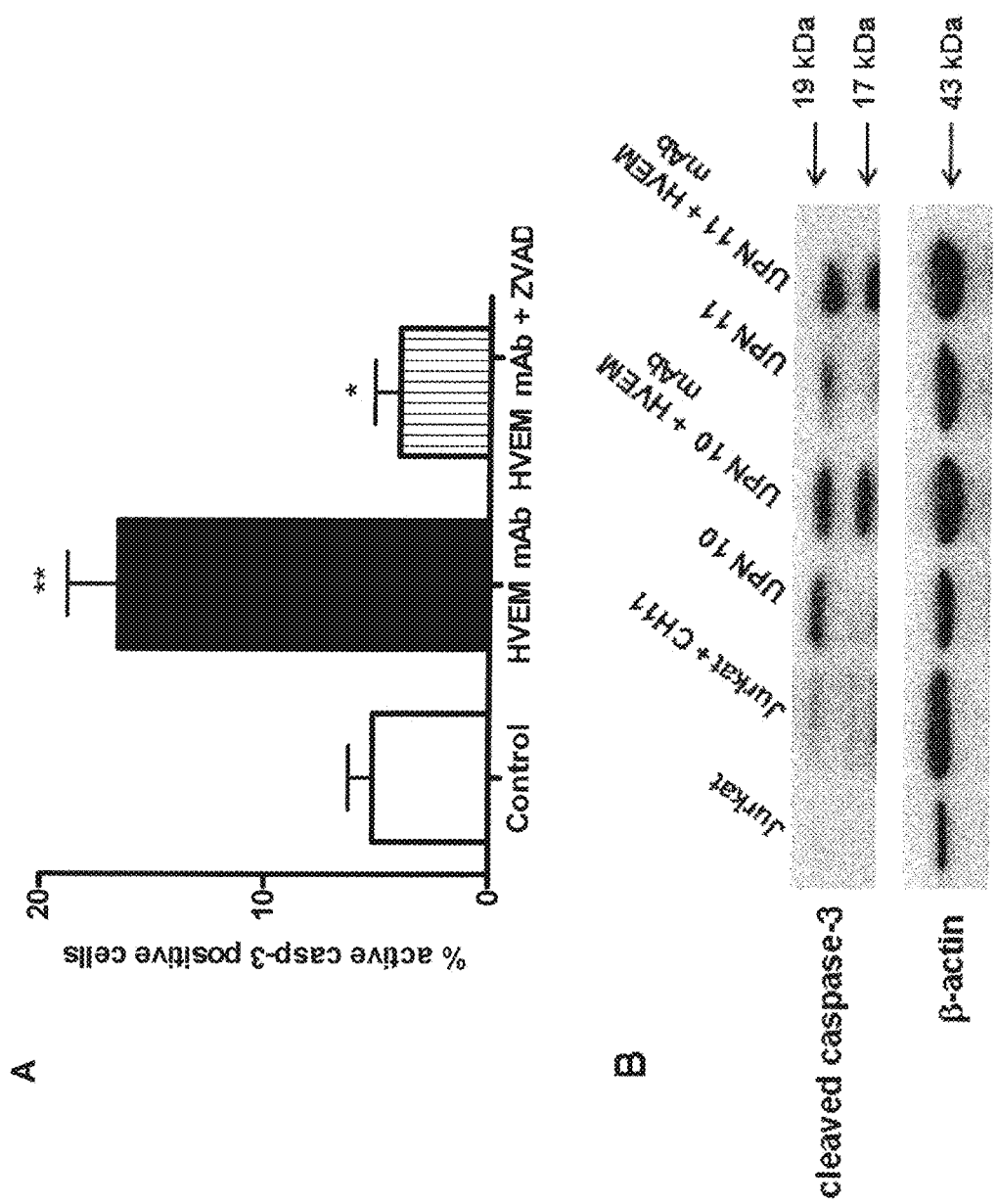

FIG. 4: HVEM mAb induces activation of caspase-3, -8 and -9

(A) B-CLL cells were pretreated or not with 20 uM of the pan-caspase inhibitor Z-VAD-FMK for 30 min at 37° C., and then either left untreated or stimulated with anti-HVEM mAb. After 24 hours of incubation, cells were collected, permeabilized and stained for active caspase-3. In parallel, cells were analysed with Annexin V/PI double staining. Data represent the mean percentage of cells positive for active caspase-3±SEM (left), and the mean percentage of dead cells±SEM (right) observed for 7 independent experiments. $*p<0.05$; $**p<0.01$. (B) B-CLL cells from two different patients were either left untreated or stimulated with anti-HVEM mAb. After 24 hours of incubation, cells were collected, and lysates were prepared. Immunoblot membranes prepared from such samples were probed for cleaved caspase-3 or β-actin (to control for protein loading), as indicated at the left of each immunoblot. Jurkat cells unstimulated or treated with the anti-Fas mAb CH11 were used as positive control. Ratios of stimulated condition vs unstimulated condition for the 19 and 17 kDa bands are respectively: JA16 (1.35-++), UPN10 (0.76-1.57) and UPN11 (1.2-1.73). (C) B-CLL cells were either left untreated or stimulated with anti-HVEM mAb for 24 hours. Cells were then incubated with specific caspase-8 or -9 fluorescent inhibitor at the indicated time points for 1 hour at 37° C., and analyzed by flow cytometry. Data represent the mean percentage of positive cells for active caspase-8 or -9 (after subtraction of the background corresponding to the untreated condition)±SEM observed for 6 different patients.

Figure 5:
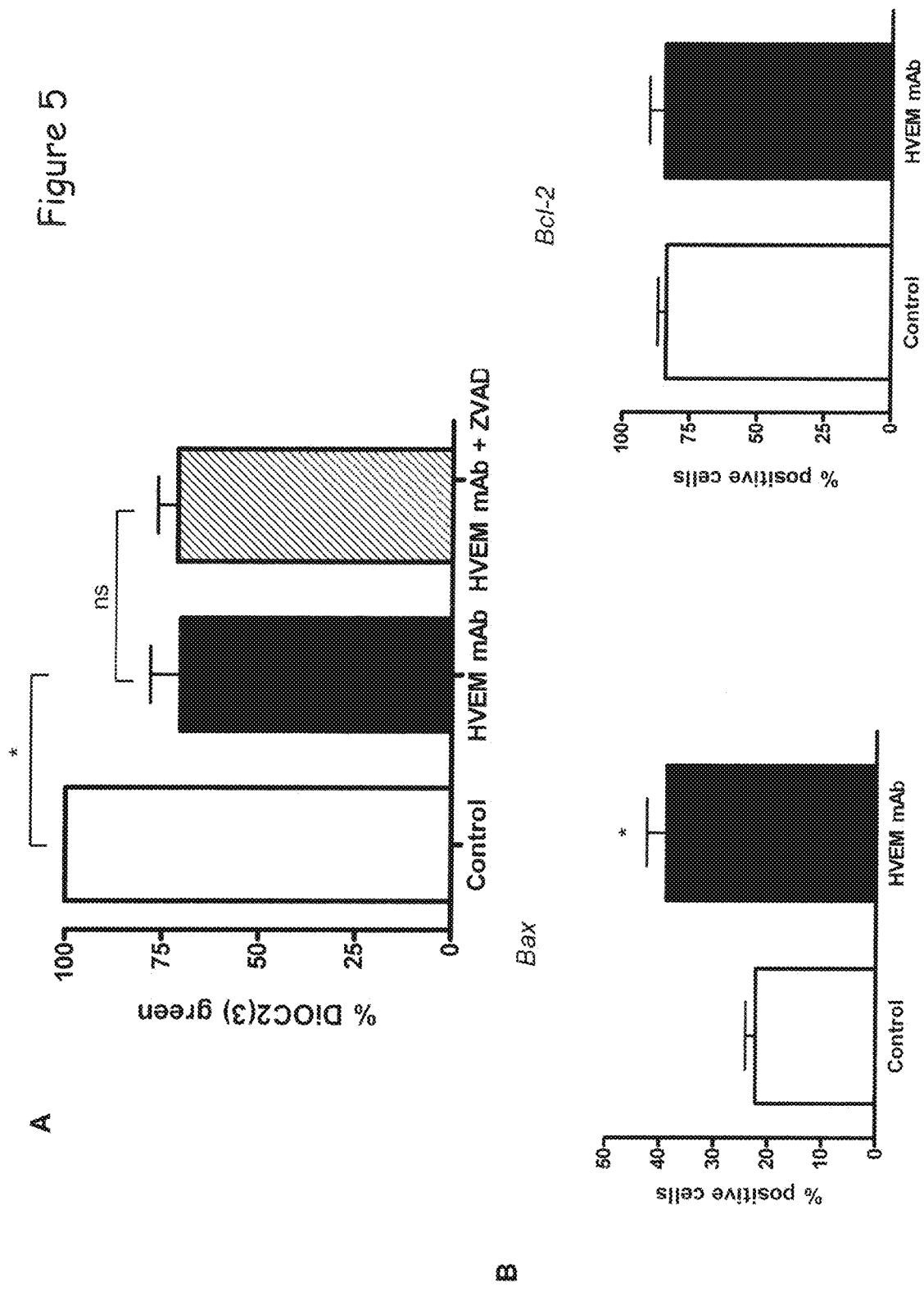

FIG. 5: HVEM mAb disrupts the mitochondrial membrane potential and increases Bax expression (A) B-CLL cells were pretreated or not with 20 μM of the pan-caspase inhibitor Z-VAD-FMK for 30 min at 37° C., and then either left untreated or stimulated with anti-HVEM mAb. After 24 hours of incubation, cells were collected, incubated with 50 nM of DiOC2(3) for 30 min at 37° C., and analyzed for the loss of mitochondrial membrane potential ($\Delta\psi m$) by flow cytometry. Data represent the mean percentage of positive cells±SEM for DiOC2(3) green fluorescence for 6 different patients, with the % of DiOC2(3) green fluorescence in the control condition set to 100%. *$p<0.05$. The positive control was the depolarizing agent CCCP (4±1% DiOC2(3) positive cells, data not shown). (B) B-CLL cells were either left untreated or stimulated with anti-HVEM mAb. After 24 hours of incubation, cells were collected, permeabilized and stained with anti-Bax or anti-Bcl-2 monoclonal antibody, and analyzed by flow cytometry. Results are expressed here as the mean percentage of positive cells (after subtraction of the background corresponding to the isotype-matched control)±SEM observed for 6 different patients. *$p<0.05$.

Figure 6:
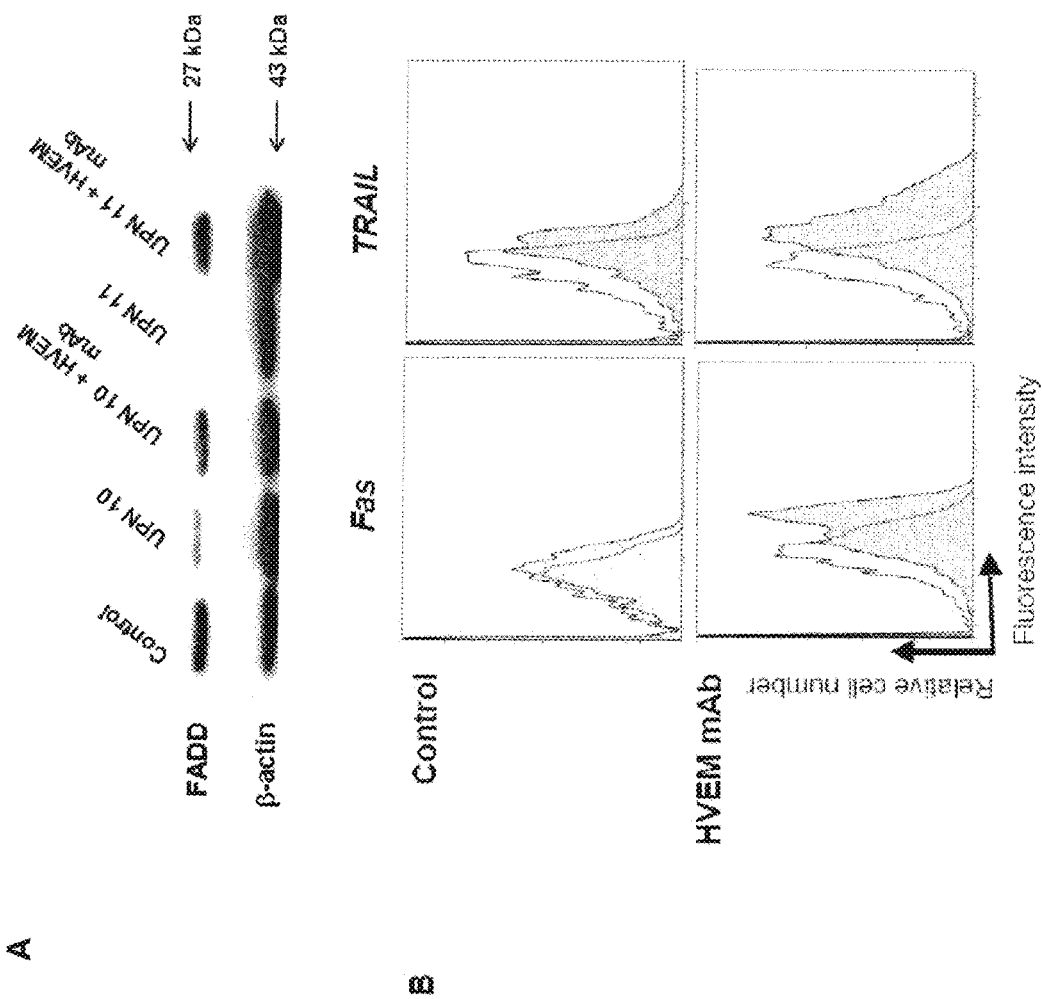
Figure 6:
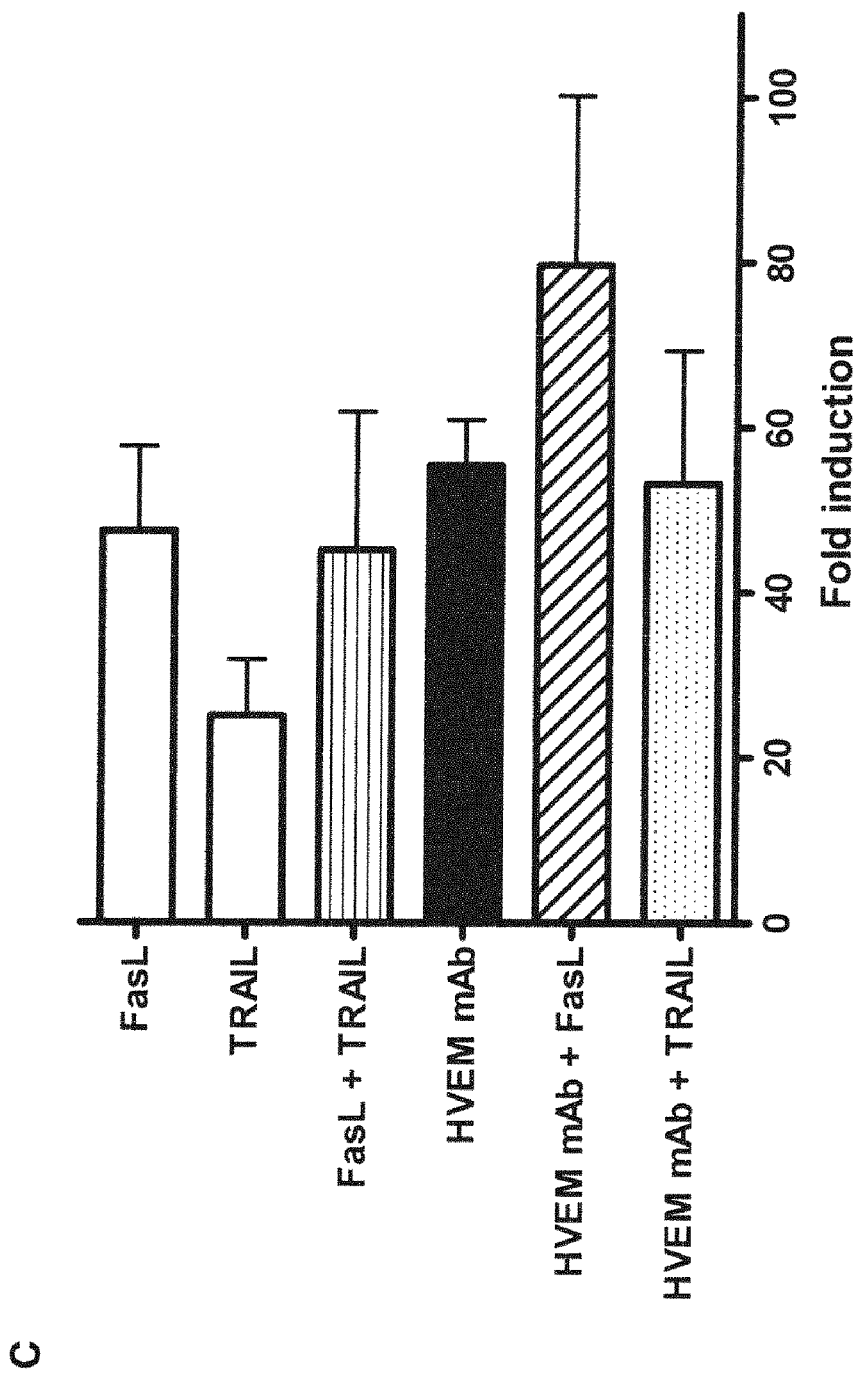
Figure 6:
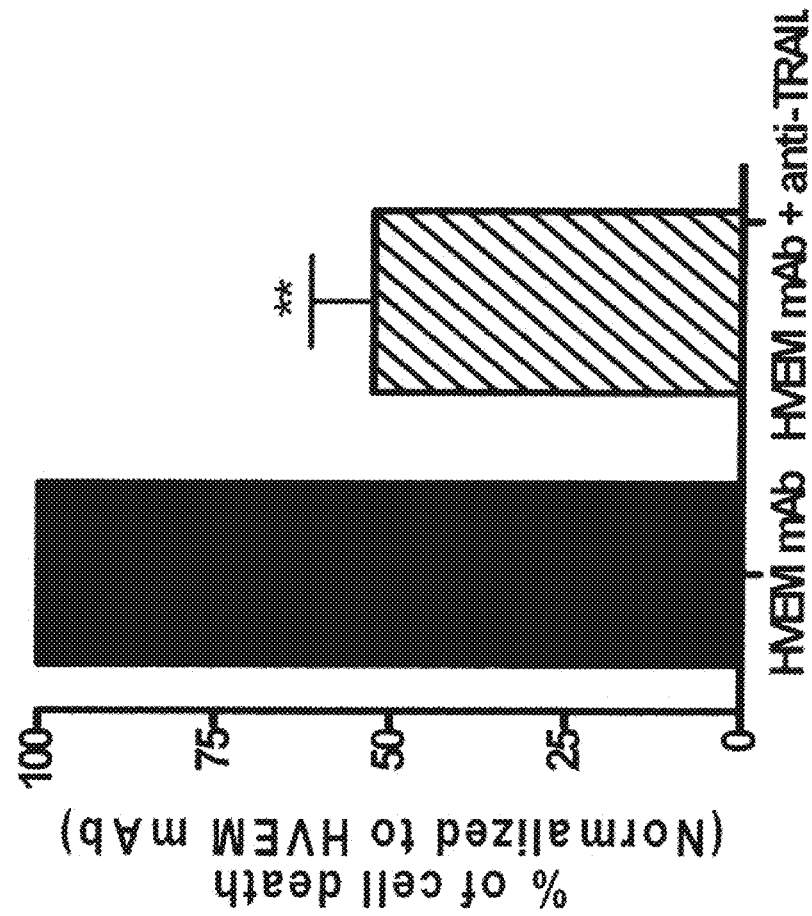

FIG. 6: HVEM-cell death increases FADD expression and partially depends on TRAIL pathway (A) B-CLL cells from two different patients were either left untreated or stimulated with anti-HVEM mAb. After 24 hours of incubation, cells were collected, and protein lysates were prepared. Immunoblot membranes prepared from such samples were probed for FADD or β-actin (to control for protein loading), as indicated at the left of each immunoblot. TF1 erythroleukemic cell line was used as positive control. Ratios of stimulated condition vs unstimulated condition for the 27 kDa band are respectively 2.39 for UPN10 and 5 for UPN11. (B) Cos cells were transfected transiently by FasL or TRAIL for 24 hours, then B-CLL cells were added, in the presence or not of HVEM mAb for 24 hours. Cells were then collected and stained with Annexin V/PI for flow cytometry analysis. Data are presented as fold induction calculated as ((percent apoptosis of treatment−percent apoptosis of untreated cells) divided by percent apoptosis of untreated cells×100) for 3 different patients. (C) B-CLL cells were left untreated or stimulated with HVEM mAb, in the presence or not of 100 ng/ml of the blocking anti-TRAIL mAb RIK-2 for 24 hours. Cells were then analysed by flow cytometry with Annexin V/PI double staining. Data represent the mean percentage of dead cells±SEM for 8 different patients, with cell death induced in HVEM mAb condition set to 100%. Cell death induced in the blocking condition was then calculated relative as: (percent apoptosis in the blocking condition divided by percent apoptosis of HVEM mAb× 100). **$p<0.01$.

Figure 7:
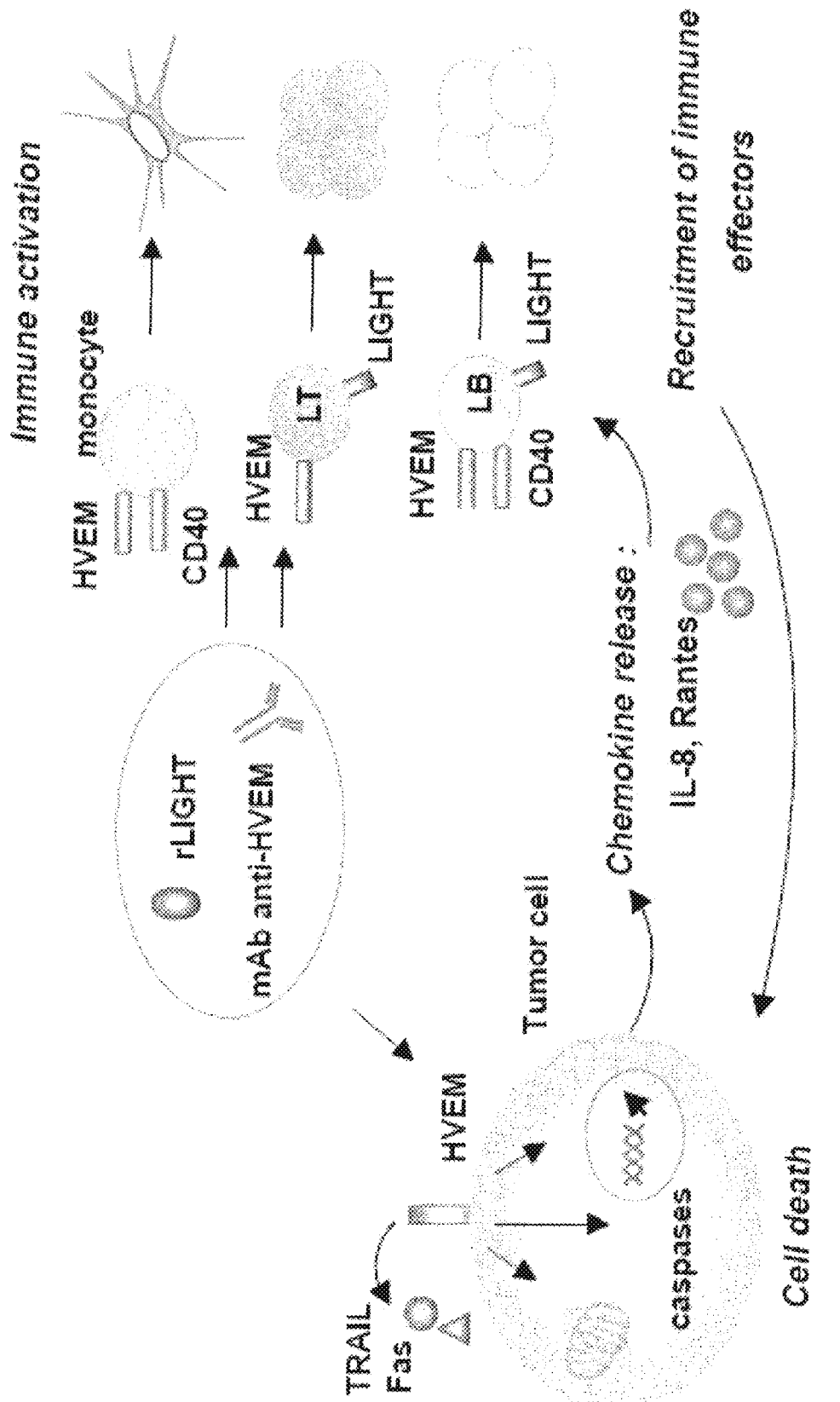

FIG. 7: Schematic mechanism of action of HVEM mAb and LIGHT

Figure 8:
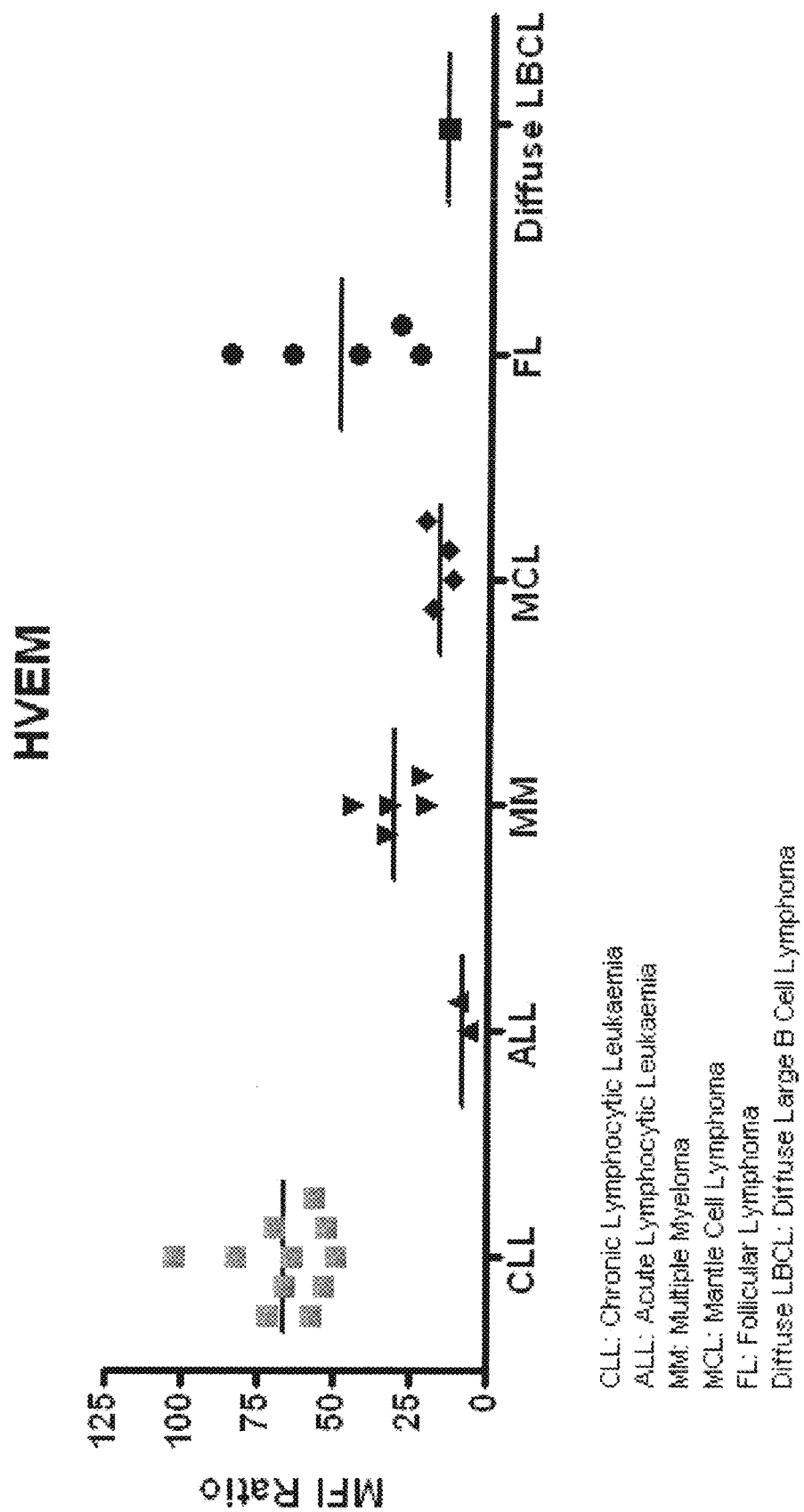

FIG. 8: Flow cytometry analysis of HVEM expression on different cell types

Figure 9:
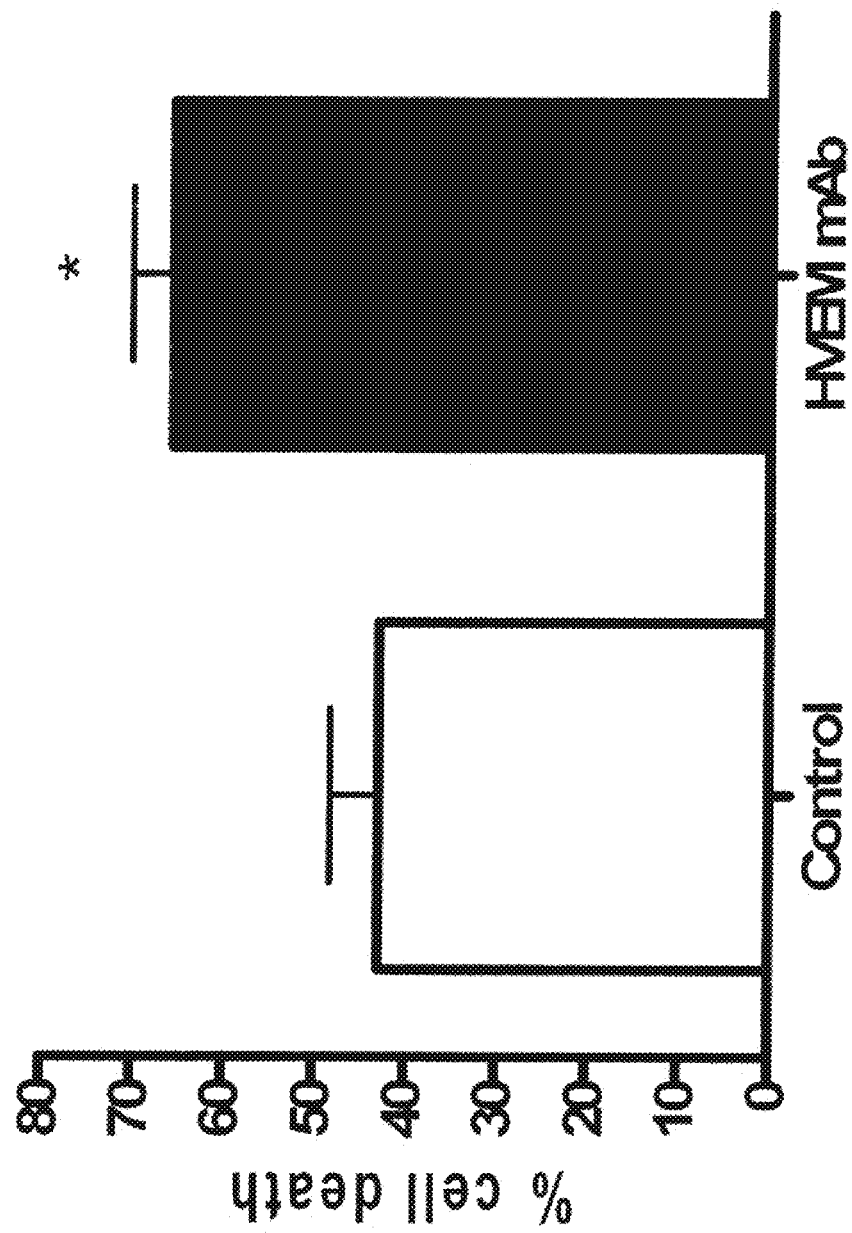

FIG. 9: Analysis of normal B cells sensitivity to HVEM triggered cell death

TABLES

Table 1: Chemokine, Cytokine & Receptor Genes Upregulated in CLL by Stimulation with HVEM mAb.

B-CLL cells were either left unstimulated or stimulated with anti-HVEM mAb before RNA extraction. RNA content was evaluated by qRT-PCR as described in material and methods section. RNA expression was considered as positive when superior to 1.5. The experiments were performed on 4 different B-CLL samples.

Chemokine, Cytokines & Receptors Genes Upregulated in CLL by Stimulation with HVEM mAb

| Chemokines | Chemokine Receptors | Cytokines | Cytokine Receptors |
|---|---|---|---|
| IL-8 | CCR4 | IL-1α | TGF-βR1 |
| MIP-1α | CXCR1 | IL-1β | |
| IP10 | XCR1 | IL-10 | |
| Eotaxin 2 | | IL-24 | |
| GRO1 | | IL-25 | |
| MCP1 | | CSF2 | |
| MCP2 | | | |

A total number of 180 cytokine, chemokine, receptor and adhesion genes were analyzed, β-actin was used to normalize cDNA concentrations.

Table 2: Characterization Summary of HVEM mAb Clones.

Fourteen mAb clones were characterized for a number of methods. This list represents a summary of a subset of data generated on 3 mAb clones. The data in this table includes the Ig isotype of the mouse heavy chain, the type of the light chain, the $EC_{50}$ value which represents the 50% saturation binding to HVEM by flow cytometry, the epitope cluster, and the ability of the mAb to induce apoptosis of CLL cells. The epitopes for this panel of mAbs represent 3 of 5 which were determined by binding studies with HVEM mutants, and competition studies with LIGHT, BTLA and HSV-gD.

Summary of HVEM mAb Clone Characterization

| mAb Clone | Isotype | EC50 (μM) | HVEM Binding | Epitope Cluster | CLL Apoptosis |
|---|---|---|---|---|---|
| HVEM4-4 | IgG2b κ | 0.12 | + | II | + |
| HVEM11-8 | IgG1 κ | 0.10 | + | V | + |
| HVEM20-4 | IgG1 κ | 0.24 | + | IV | + |

TABLE 3

WHO classification of B-cell lymphoid neoplasms (Jaffe, E. S. et al., 2004).

Precursor B-cell neoplasm

Precursor B-lymphoblastic leukemia/lymphoma
Mature B-cell neoplasms

Chronic lymphocytic leukemia/small lymphocytic lymphoma
Variant: with plasmacytoid differentiation or monoclonal gammopathy
B-cell prolymphocytic leukemia
Lymphoplasmacytic lymphoma
Splenic marginal zone B-cell lymphoma (±villous lymphocytes)
Hairy cell leukemia
Variant: hairy cell variant
Plasma cell myeloma/plasmacytoma
Extranodal marginal zone B-cell lymphoma of MALT type
Nodal marginal zone B-cell lymphoma (±monocytoid B cells)
Follicular lymphoma

TABLE 3-continued

WHO classification of B-cell lymphoid
neoplasms (Jaffe, E. S. et al., 2004).

Variants:
Cutaneous follicle center lymphoma
Diffuse follicle center lymphoma
Mantle cell lymphoma
Variant: blastoid
Diffuse large B-cell lymphoma
Subtypes:
Mediastinal large B-cell lymphoma
Intravascular large B-cell lymphoma
Primary effusion lymphoma
Morphologic variants
Centroblastic
Immunoblastic
Anaplastic large B-cell
T-cell/histiocyte-rich
Plasmablastic
Lymphomatoid granulomatosis-type
Burkitt's lymphoma/Burkitt's cell leukemia
Morphologic variants
Classical
Atypical
With plasmacytoid differentiation (AIDS-associated)
Subtypes (clinical and genetic)
Endemic
Sporadic
Immunodeficiency-associated
B-cell proliferations of uncertain malignant potential Lymphomatoid granulomatosis (grades 1, 2 and 3)
Post-transplant lymphoproliferative disease

TABLE 4

WHO classification of T-cell and NK-cell lymphoid
neoplasms (Jaffe, E. S. et al., 2004).

Precursor T-cell neoplasm

Precursor T-lymphoblastic lymphoma/leukemia
Mature (peripheral) T-cell and NK-cell neoplasms T-cell prolymphocytic leukemia
Morphologic variants: small cell, cerebriform cell
T-cell granular lymphocytic leukemia
Aggressive NK-cell leukemia
Elastic 'NK-cell' lymphoma
Adult T-cell leukemia/lymphoma (HTLV-1+)
Clinical variants
Acute
Lymphomatous
Chronic
Smoldering
Hodgkin-like
Extranodal NK/T-cell lymphoma, nasal type
Enteropathy-type T-cell lymphoma
Hepatosplenic T-cell lymphoma
Subcutaneous panniculitis-like T-cell lymphoma
Mycosis fungoides/Sezary syndrome
Variants
Pagetoid reticulosis
MF-associated follicular mucinosis
Granulomatous slack skin disease
Primary cutaneous CD30+T-cell lymphoproliferative disorder
Variants
Lymphomatoid papulosis (type A and B)
Primary cutaneous anaplastic large-cell lymphoma
Borderline lesions
Peripheral T-cell lymphoma, not otherwise characterized
Morphologic variants: lymphoepithelioid (Lennert's), T-zone
Angioimmunoblastic T-cell lymphoma
Anaplastic large cell lymphoma, (ALK+/ALK−)
Morphologic variants: lymphohistiocytic, small cell

EXAMPLES

Example 1

LIGHT and Anti-HVEM Antibodies Induce Both Apoptosis of Chronic Lymphocytic Leukemia B Cells and Chemokine Release Through Interaction with HVEM Abstract By studying the effect of LIGHT in the global transcriptional profile of a lymphoid malignancy, we found that HVEM but not LTβR stimulation induced a significant increase of chemokine genes, such as IL-8, and an unexpected upregulation of apoptotic genes. This apoptotic transcriptional profile was associated with a killing effect, as LIGHT or anti-HVEM mAb, until yet known to costimulate T- and B-cell activation, clearly induced chronic lymphocytic leukemia (CLL) cell death. This cell death was associated with activation of caspase-3, -8 and -9, decrease in mitochondrial membrane potential, and upregulation of the proapoptotic protein Bax. Moreover, HVEM stimulation induced upregulation of the death molecules TRAIL and Fas, and the HVEM-mediated apoptotic mechanism seems to depend in part of the TRAIL pathway. HVEM stimulation both induced apoptosis of B-CLL cells and might participate to the recruitment of immune effectors through direct chemokine production by leukemic cells. HVEM function was mainly dependent on one of its ligands, LIGHT since other ligands like gD HSV1 and BTLA were mainly ineffective. In conclusion, these results show a novel, as yet unknown killing effect of LIGHT or anti-HVEM antibodies through HVEM in a lymphoid malignancy, combined with chemokine release, that represents an additional tool for cancer immunotherapy.

Material and Methods

Cells

This study was approved by the review board of the Institut Paoli-Calmettes, Marseille, France. After informed consent in accordance with the Declaration of Helsinki, peripheral-blood samples were obtained from untreated patients diagnosed with chronic lymphocytic leukemia (CLL) on the basis of clinical and immunophenotypic criteria. The mononuclear cells were isolated by density gradient centrifugation (Lymphoprep) and viably frozen in fetal bovine serum (PAN Biotech) containing 10% dimethyl sulfoxide (SIGMA).

Stably transfected cells L-CD40L, L-LIGHT, L-CD40L/LIGHT, L-GpD and L-BTLA were obtained by transfecting by electroporation (960 μF, 220 V, BIO RAD Gene Pulser and Capacitance extender) LTK murine fibroblasts with pcDNA3.1 vector (Invitrogen, Groningen, The Netherlands) encoding human CD40L, LIGHT, GpD or BTLA respectively. Stably transfected cells selected by resistance to antibiotic were selected by three rounds of FACS sorting. Expression of the molecule of interest was verified by flow cytometry using a phycoerythrin-conjugated monoclonal antibody (mAb) (R&D Systems) . . . CD32-transfected fibroblasts were a kind gift from Schering-Plough (Dardilly, France). Transient transfected Cos-FasL cells and Cos-TRAIL cells were generated by respectively transfecting monkey kidney Cos cell line with.

Co-Culture of B-CLL Cells with Transfected L-Cells or Antibodies

B-CLL cells were co-cultured with 50 grays-irradiated L-cells transfected with human LIGHT, CD40L, GpD, or BTLA, at a ratio of 1 transfectant for 10 B-CLL cells for 24 hours. Cells were also treated with 30 μg/ml anti-HVEM monoclonal antibody (mAb) or 10 μg/ml therapeutic Rituximab antibody, in 24-well plates for 24 hours. In some experiments, B-CLL cells were first preincubated with 20 μM of the pan-caspase inhibitor N-carbobenzoxy-Val-Ala-Asp fluoromethyl ketone (Z-VAD-FMK) (BD Biosciences), or with blocking anti-TRAIL mAb RIK-2 (BD Biosciences). Then, cells were collected, checked for viability, and re-suspended in fresh medium before use.

Immunofluorescence Analysis of Cell-Surface Antigens

Cell surface analysis of B-CLL cells was performed through flow cytometry with the use of a FACSCanto cytometer and FACSDiva software (Becton Dickinson, Mountain View, Calif.). B-CLL cells were immunostained at 4° C. for 30 minutes, with the following mAbs: fluorescein isothiocyanate (FITC)-conjugated anti-CD19 (Beckman Coulter), FITC-conjugated anti-HVEM (BD Biosciences), phycoerythrin (PE)-conjugated anti-LTβR(R&D), FITC-conjugated anti-Fas (CD95) (Beckman Coulter), PE-conjugated anti-TRAIL (BD Biosciences), PE-conjugated anti-FasL (Biolegend), PE-conjugated anti-DR4 or PE-conjugated anti-DR5 (R&D). FITC- or PE-labeled isotype-matched Ig's were used as negative controls. After 2 washings in phosphate-buffered saline (PBS) plus 2% FCS, cells were analyzed by flow cytometry.

Annexin V/PI Staining

Following stimulation, cell death was analyzed by Annexin V-Cy5 (BD Biosciences) and Propidium Iodide (PI) double staining (BD Biosciences). Annexin V specifically binds to phosphatidyl serine, a phospholipid that becomes exposed on the surface of cells undergoing apoptosis. Dual staining with PI enables the identification of early apoptotic cells that have not yet lost their membrane integrity. Briefly, $5\times10^5$ cells were washed once with phosphate-buffered saline (PBS) 1% FCS and resuspended in 100 μl 1× binding buffer (BD Biosciences) with 5 μl Annexin V-Cy5 for 10 min at room temperature in the dark. Then 200 μl of 1× binding buffer and 3.5 μl of PI were added, and cells were incubated for 5 min at RT in the dark. Cells were then analyzed on a FACSCanto cytometer (Becton-Dickinson). Data analysis was performed with FACSDiva software (Becton-Dickinson). Dead cells were measured as the percentage of Annexin V and PI double positive cells.

Determination of Caspase, Bax and Bcl-2 Activation by Flow Cytometry

Caspase 8 and caspase 9 activities were measured at different times using the following cell-permeable fluoresceinated caspase inhibitors: FAM-LETD-FMK (caspase-8 inhibitor) and FAM-LEHD-FMK (caspase-9 inhibitor) (CaspGLOW kits, Biovision). Cells were stained for 1 hour at 37° C. in the dark, then washed, resuspended in 0.5 mL buffer, and immediately analyzed by flow cytometry on a FACSCanto cytometer (Becton-Dickinson).

To detect activated intracellular caspase-3, Bcl-2 and Bax, cells were permeabilized using cytofix/cytoperm buffer (BD Biosciences), and stained with PE-conjugated anti-active caspase 3 monoclonal antibody (BD Biosciences), anti-Bax monoclonal antibody (Santa Cruz Biotechnology, Inc.) or anti-Bcl2 monoclonal antibody (BD Biosciences), and then analysed by flow cytometry.

Determination of Mitochondrial Membrane Potential (Δψm)

Changes in the mitochondrial membrane potential was measured with the cationic cyanine dye DiOC2(3). After stimulation, B-CLL cells were washed, resuspended with 1 ml PBS, and supplemented with 5 μl of 10 μM DiOC2(3) solution, incubated for 30 min (Molecular Probes) at 37° C. in the dark. Cells were washed again, resuspended with 500 μl PBS and analyzed by flow cytometry. DiOC2(3) fluorescence decreases when cells undergo apoptosis. The positive control was CCCP.

Cytokine and Chemokine Production

Supernatants were harvested after a 24 hours stimulation. The cytokines were measured using the Cytometric Bead Array (CBA) Human Chemokine kit (BD Biosciences), a multiplexed based immunoassay which allows quantitative detection of several cytokines (IL-8/CXCL8, RANTES/CCL5, MIG/CXCL9, MCP-1/CCL2, IP-10/CXCL10) in the same sample, as described by the manufacturer. The IL-8 was also quantified using an immuno-enzymatic assay following the protocol described by the manufacturer, with a sensitivity of 3.5 pg/ml (R&D systems).

Western Blotting Analysis

B cells ($10^7$ cells/sample) from CLL patients were incubated with or without anti-HVEM mAbs for 24 hours. For preparation of cells lysates, the cells were collected by centrifugation at 250 g for 10 minutes at 4° C., washed once in ice-cold phosphate-buffered saline (PBS), and then lysed in NP-40 lysis buffer (50 mM HEPES (pH 7.4), 150 mM NaCl, 10 mM NaF, 10 mM iodoacetamide, 1% NP-40, 1 mM phenylmethylsulfonyl fluoride, 1 μg/ml protease inhibitor cocktail) for 15 minutes on ice. The lysate was cleared from insoluble debris by centrifugation at 21 000 g for 10 min at 4° C., and the supernatant was stored at −20° C. After SDS-PAGE separation in denaturing conditions, the proteins were transferred onto nitrocellulose membranes blocked overnight at 4° C. with 5% milk in tris buffer saline (TBS), and then stained with anti-cleaved caspase 3 (Cell Signaling) or anti-FADD (produced in our laboratory) antibody. The bands were then visualized with horseradish peroxidase (HRP) conjugated anti-mouse or anti-rabbit IgG, and Western blot chemiluminescence reagent (West Pico, Pierce). β-actin expression was determined on the same blots after stripping for 30 minutes at 60° C. with buffer containing 2% SDS. Each band was scanned (Powerlook 1000, Umax) and quantified using the Phoretix 1D Advanced software (Nonlinear Dynamics). Data were then converted to a fold change ratio obtained by dividing the stimulated condition values normalized with β-actin by values determined for unstimulated cells normalized with β-actin.

Quantitative RT-PCR

Before RNA isolation, all cells were selected for their ability to be killed by HVEM mAb. QRT-PCR analysis was performed with the Applied Biosystems 7900HT Fast Real-Time PCR system. Briefly, total RNA was isolated from B-CLL cells using the standard TRIzol reagent protocol (Invitrogen Life Technologies) one day poststimulation. RNA were reverse transcribed using oligo(dT)15. Then, the two following supports were used. In the first method, eighty-seven gene targets each coding for adhesion, migration, cytokines, or apoptosis molecules were spotted on optical plates (Microamp Fast Optical 96 well, Applied Biosystems). QRT-PCR was performed in a 20 μl reaction containing 2×SYBR Green reagent, 200 nM primers and 0.5 μl cDNA (equivalent to 10 ng of total RNA) in each well. Thermal cycle conditions were 15 s at 95° C., 60 s at 60° C. for 40 cycles. In the second method, ninety-six gene targets each coding for immune molecules were spotted into TaqMan low-density array (Immune Panel Microfluidic Card, Applied Biosystems). Briefly, 5 ul cDNA (equivalent to 100 ng of total RNA) was mixed with 100 μl of 2×TaqMan universal Mix (Applied Biosystems) and loaded into one sample port. Thermal cycle conditions were: 30 s at 97° C., 60 s at 59.7° C. for 40 cycles. Capture of fluorescence was recorded on the ABI Prism 7900HT scanner, and the Ct (threshold cycle) was calculated for each assay using Sequence Detection System Software 2.1 (Applied Biosystems). Normalization of quantitative-PCR assays was conducted using β-actin as endogenous control. Data were then converted to a fold change ratio described with the formula: $2^{-\Delta\Delta ct}$, where $\Delta Ct=Ct$ target$-Ct$ endogenous control, and $\Delta\Delta Ct=\Delta Ct$ stimulated condition$-\Delta Ct$ unstimulated condition.

Statistical Analysis

Results were compared by the non parametric Wilcoxon signed-rank test, to evaluate any statistically significant difference between HVEM mAb treated condition and untreated condition. Differences were considered significant when p<0.05. P values are indicated in the legends of figures.

Results

Expression of HVEM and LTβR on Haematopoietic Malignancies

In order to study the role of LIGHT in haematopoietic malignancies, it is therefore important to define the level of expression of its two receptors HVEM and LTβR. Previous results by Costello R T and al in our lab showed that HVEM was expressed in a number of lymphoid malignancies, particularly on leukemias of B origin, with high intensity in all the chronic lymphocytic leukemias (CLL) and all the mantle cell lymphomas tested (MCL), and often observed in acute lymphoblastic leukemias (ALL). As shown in FIG. 1a, we confirmed that HVEM was strongly expressed in 9 CLL and 2 MCL tested, whereas HVEM expression was weak in 2 leukemias of myeloid origin (acute myeloid leukemias, AML). In sharp contrast, LTβR was expressed in AML, but absent in MCL and infrequent or low in CLL. As seen in FIG. 1b, in the 9 CLL tested, HVEM was expressed at uniformly high levels, and LTβR was either weakly or not expressed.

HVEM Stimulation Induces Overexpression of 12 Chemokines and Apoptotic Genes Among the 322 Genes Tested B-CLL was therefore a study model with a predominant expression of HVEM and a weak or absent LTβR expression. Therefore, to explore the impact of LIGHT on this lymphoid malignancy, we stimulated B-CLL cells with an anti-HVEM monoclonal antibody (HVEM mAb) during 24 hours. After RNA preparation, we performed a real-time quantitative PCR global analysis of the expression of 322 genes coding for chemokines, chemokine receptors, cytokines, and molecules involved in essential mechanisms of the cells as adhesion, migration or apoptosis. As seen in FIG. 2, among these 322 genes tested, our results showed that 21 genes were not expressed at all in the CLL patients tested, 80 genes were weakly detected, and 221 genes were expressed with correct transcript level. All these genes were not modified by HVEM stimulation. Indeed, among the 322 genes tested, only 12 were significantly overexpressed following HVEM stimulation, suggesting a focused transcriptional profile for LIGHT on B-CLL cells. HVEM stimulation up-regulated the expression of 3 genes coding for chemokines: IL-8 (Interleukin-8), IP10 (IFN-inducible protein 10) and CCR4 (Chemokine (C—C motif) receptor 4), each critical for the recruitment of immune effectors. The increase of these genes after HVEM stimulation was statistically significant with the Wilcoxon signed-rank test (p value <0.01). This pro-inflammatory profile was not surprising since HVEM-LIGHT signalling was already associated with IL-8 and TNF-α production in monocytic cell lines. To complete, we also analysed if this transcriptional effect was associated with chemokine release at the protein level. We measured the chemokine production in stimulated B-CLL cells by cytometric bead array or Elisa, and we showed that HVEM induced a major significant release of both chemokines IL-8 from 3 to 10 fold in 12 different patients (p<0.001), and Rantes in 9 patients (Regulated on activation, normal T-cell expressed and secreted) (p<0.01). No significant increase in the release of IP10 was observed. Surprisingly, the 9 other genes significantly induced after HVEM stimulation all corresponded to genes coding for apoptotic proteins, most of them pro-apoptotic: Bcl-XS, Bid, FasL, with p<0.01; BNIP3, CARD11, Cytochrome c, p53, with p<0.05; and some others belonging to anti-apoptotic subgroup: BIRC4, and IEX-1, with p<0.05. LIGHT was already described to induce apoptosis of adenocarcinoma in vitro, but it was due to its interaction with LTβR, and this pro-apoptotic effect needed the presence of IFN-γ.

LIGHT and Anti HVEM mAb Induces Death of B-CLL Cells

We sought to determine if this apoptotic transcriptional profile was correlated with a function in vitro. First, B-CLL cells were cocultured with CD32- or LIGHT-transfected L-cells during 24 hours, then the percentage of apoptotic cells was measured by Annexin V/PI double staining. Apoptotic cells include Annexin V+/PI− (early apoptotic) and Annexin V+/PI+ (late apoptotic/necrotic) populations. We found that stimulation by LIGHT effectively induced cell death of 41% of the B-CLL cells compared to 8% with the CD32 control condition (spontaneous cell death) on this representative experiment (FIG. 3a). These results were reproduced in 15 B-CLL samples. Then, we stimulated leukemic cells with HVEM mAb during 24 hours. We had previously shown that this antibody blocked the interaction between HVEM and its ligand LIGHT (data not shown). FIG. 3b shows both LIGHT and anti-HVEM mAb were able to induce CLL cell death, with 42±3% and 52±3% dead cells respectively, compared to 22±2% in the CD32 control condition, corresponding to highly statistically significant (p<0.001) 1.9- and 2.4-fold increase. Thus, the apoptotic transcriptional profile caused by LIGHT or HVEM triggering on CLL was correlated with a death-inducing function in vitro. Although the pro-apoptotic effect of LIGHT was described to be mediated by LTβR in adenocarcinoma, in our study this effect is due to the "costimulatory" molecule HVEM. A role for HVEM was further inferred by the inability of rhLTα$_1$β$_2$, the other LTβR ligand, to induce CLL cell death. As further corroborating evidence for the involvement of HVEM, B-CLL cells which did not express LTβR (FIG. 1a) were nevertheless killed by anti-HVEM mAb. In addition, another B cell lymphadenopathy, MCL, which is also negative for the expression of LTβR, was killed by treatment with LIGHT (data not shown). To note, LIGHT or anti-HVEM mAb-induced CLL cell death does not require priming of the cells with IFN-γ (data not shown).

Actual treatment options for patients with CLL are relatively limited, and correspond to chemotherapy, allogeneic stem cell transplantation, or passive immunotherapy with monoclonal antibodies. Anti-HVEM mAb and Rituximab were compared for their effectiveness in inducing CLL cell death (FIG. 3b). The HVEM-induced CLL cell death compared favorably with that of the pan-B cell therapeutic mAb rituximab, with 52±3% and 46.2±6% of dead cells respectively.

In addition, several ligands were identified last years for HVEM: LIGHT, but also gpD and BTLA. We compared the effects of the different HVEM ligands to efficacy of HVEM mAb, B-CLL cells were co-cultured with CD32-, LIGHT-, GpD-, or BTLA-transfected L-cells during 24 hours, then the percentage of apoptotic cells was measured by Annexin V/PI double staining. CD40L-transfected L-cells were used as "non ligand" negative controls. HVEM mAb cell death was set to 100%. As seen in FIG. 3c, L-LIGHT cells had the more significant closer effect compared to HVEM mAb (70±15%, p<0.05), L-GpD cells had a weak effect (41±6% of HVEM mAb, p<0.05), and L-BTLA cells had no significant efficacy compared to HVEM mAb (32±10%). L-CD40L cells used as a negative control cells had no effect on B-CLL cell death (24±9% of HVEM mAb). We also tested L-CD40L/LIGHT because we had previously shown that these two molecules act in cooperation for B lymphocyte proliferation. Here, L-CD40L/LIGHT cells did not affect L-LIGHT killing of B-CLL cells, thus CD40L and LIGHT did not seem to act in cooperation on cell death.

HVEM-Mediated Apoptosis Involves Caspase-3, -8 and -9 Activation

Apoptosis induced by the TNFR family members such as Fas, TNFR1, and the TRAIL receptors DR4 and DR5 has been described to depend on the presence of the intracytoplasmic death-domain. The death-domain is however absent from HVEM. In order to define HVEM-mediated apoptosis mechanisms, we first analyzed caspase activation. By intracytoplasmic staining, we showed in FIG. 4a that stimulation of B-CLL cells by anti-HVEM mAb results in statistically significant caspase-3 activation (16.5±2% positive cells for HVEM mAb condition vs 5.2±1% for the control condition, p<0.01). This observation was confirmed by western blotting analysis, with an increase of the 19 and 17 kDa active forms (FIG. 4b). FIG. 4a also shows that caspase-3 activation induced by HVEM mAb is completely abrogated by pretreatment with the pan-caspase inhibitor Z-VAD-FMK (4±1% positive cells, left panel). In contrast, pretreatment with Z-VAD-FMK only partially blocked Annexin V/PI staining observed after HVEM stimulation (38±4% and 45±5% of dead cells respectively, right panel). In addition, we analyzed by flow cytometry (FIG. 3c) the activation of the effectors caspases 8 and 9. Both caspase-8 and caspase-9 were activated in response to treatment of CLL cells by anti-HVEM mAb. Interestingly, caspase-8 and caspase-9 were activated with similar kinetics, with 0±1.5% (t=3 h), 5.4±2.5% (t=6 h), 16±3.2% (t=12 h), 24.8±3.1 (t=24 h) for caspase-8, and 0.88±2.1% (t=3 h), 4.7±2.6% (t=6 h), 18.4±4.1% (t=12h), 31.4±5.1 (t=24 h) for caspase-9.

HVEM-Mediated Apoptosis Disrupts the Mitochondrial Membrane Potential ($\Delta\psi m$) and Increases Bax Expression Mitochondrial membrane depolarization is part of the "intrinsic" pathway of apoptotic mechanisms. FIG. 5a shows that treatment of B-CLL cells with anti-HVEM mAb resulted in a loss of the mitochondrial membrane potential, as assessed by the significant decreased of the DiOC2(3) green fluorescence (70±8% in activated cells with resting cells set to 100%, p<0.05). Interestingly, the HVEM-mediated mitochondrial depolarization was not inhibited by the pan-caspase inhibitor Z-VAD-FMK (71±5% DiOC2(3) positive cells), suggesting that this step is independent of caspase activation.

The balance between Bax and Bcl-2 proteins is important for the maintenance of mitochondrial activity. Bax proapoptotic effects are counter-acted by the antiapoptotic function of Bcl-2. Using flow cytometry analysis, we showed that in resting condition, Bcl-2 was highly expressed in B-CLL cells as it was described in previous studies. HVEM stimulation did not change Bcl-2 expression, but in contrast, induced a statistically significant increase in Bax cytosolic levels (FIG. 5b) (39±4% positive cells in activated condition vs 22±2% in resting condition). This increase may be associated with the mitochondrial membrane depolarization described above.

HVEM-Cell Death Increases FADD Expression and Partially Depends on TRAIL Pathway Since HVEM is devoid of a death domain, the pathways involved in the HVEM-mediated cell death are unclear. Based on the known mechanisms of apoptosis, we analyzed the expression of FADD, the major adaptor molecule involved in Fas and TNFR mediated cell death. Interestingly, treatment of B-CLL cells with anti-HVEM mAb caused a major increase in FADD expression by western blotting analysis (FIG. 6). The stimulation caused an important fold induction of the 27 kDa band for the two figured patients (2.39 for UPN10 and 5 for UPN11).

Then we examined whether cell death induced by HVEM ligation could be indirect through other TNF receptors or ligands activation. We analysed B-CLL cells for expression of death receptors and their ligands (Fas and FasL, DR4-DR5 and TRAIL) before and after HVEM stimulation (FIG. 6b). The expression levels of each of these molecules were negligible on each of the samples (n=5) before stimulation. Expression of DR4, DR5, and FasL did not change after HVEM stimulation. In contrast, HVEM ligation induced a significant increase in TRAIL expression (p<0.05) with a pretreatment mean MR value of 179±58 to 375±81 after treatment; and a non significative increase of Fas, with pretreatment mean MFI 70±22 to 104±24. To note, TRAIL mRNA figured among the 322 genes that we tested by QRT-PCR and although TRAIL gene was expressed in CLL, it was not modified following HVEM stimulation, suggesting a post-transcriptional modification To address if HVEM cell death could be affected by FasL or TRAIL, we generated artificial cytotoxic effectors cells from Cos cells that expressed FasL, TRAIL, or both FasL and TRAIL. Expression of both FasL and TRAIL following transient transfection was verified by flow cytometry (data not shown). In addition, the transfected effector cells were examined for their capacity to induce apoptosis of Jurkat T cells that expressed both Fas and DR5. We cocultured each of Cos-effector cell populations with B-CLL cells in presence or absence of HVEM mAb for 24 hours. We found that Cos-FasL, Cos-TRAIL, Cos-FasL/TRAIL induced apoptosis of 47±10%, 25±7%, 45±17% of B-CLL cells respectively, compared to control condition, within 24 hours of coculture. Combination of HVEM mAb with Cos-FasL effector cells induced killing of B-CLL cells that seemed higher than that observed with HVEM mAb alone (80±20% and 55±5% respectively). In contrast, Cos-TRAIL effector cells added to HVEM mAb did not induce more apoptosis than HVEM mAb alone (53±16% compared to 55±5% respectively). These data suggest that HVEM and FasL induced killing of B-CLL cells through different pathways that could synergize whereas HVEM and TRAIL pathways could involve shared mediators.

In addition, we examined the effect of a blocking anti-TRAIL mAb on HVEM-induced cell death. B-CLL cells were preincubated with this blocking mAb or not, then treated with HVEM mAb within 24 hours and evaluated for Annexin V/PI staining We found that HVEM killing of CLL was significantly blocked by anti-TRAIL mAb, partially for 7 patients and totally for 1 patient tested (52±9% of dead cells in blocking condition vs 100% in HVEM mAb condition; p<0.01), suggesting that HVEM cell death pathway could at least partially involve TRAIL activation.

Discussion

In this study we highlight a novel role for HVEM and LIGHT on anti-tumor response. In this study we investigated the effects of LIGHT in hematopoietic malignancies and we chose to focus on B-CLL, given our previous results on the importance of LIGHT in the physiology of B lymphocytes. The surface expression analysis of the receptors of LIGHT showed that HVEM was expressed at high levels in B-CLL cells. In sharp contrast, LTβR expression was weak or infrequent; as a result we could consider CLL as a model with a predominant HVEM expression. Consequently, to explore the impact of LIGHT in this lymphoid malignancy, we treated B-CLL cells with an anti-HVEM mAb and we performed a QRT-PCR global analysis of the expression of a large panel of genes coding for chemokines, cytokines, and key molecules involved in adhesion, migration or apoptosis. Among the 322 genes tested, only 12 were significantly overexpressed following HVEM stimulation, suggesting a focused transcriptional profile for HVEM on B-CLL cells. HVEM ligation up-regulated the expression of 3 genes coding for chemokines: IL-8 (Interleukin-8), IP10 (IFN-inducible protein 10) and CCR4 (Chemokine (C—C motif) receptor 4), each critical for the recruitment of immune effectors. IL-8 is one of the major mediators of the inflammatory response, it functions as a chemoattractant, and is also a potent angiogenic factor; IP10 is implicated in chemoattraction for monocytes and T cells, promotion of T cell adhesion to endothelial cells and antitumor activity; and CCR4 is the receptor for TARC (thymus and activation-regulated chemokine) and MDC (macrophage derived-chemokine) produced in secondary lymphoid organs. We completed these results by measuring the chemokine production in response to HVEM, and we confirmed that HVEM induced a significant release of both IL-8 and Rantes (chemotactic for T cells, eosinophils, and basophils, and plays an active role in recruiting leukocytes into inflammatory sites). The production of IL-8 seems to be a key element in HVEM response, since it was described in several cell lines, including monocytes, neutrophils, and here in leukemic cells. Before analysing this large transcriptional response to HVEM stimulation, we could expect an upregulation of genes associated with immune activation, given the established functions of LIGHT and its receptor HVEM in costimulatory responses. But surprisingly, the 9 other genes significantly induced after HVEM stimulation all corresponded to genes coding for apoptotic proteins, most of them pro-apoptotic: Bcl-XS, Bid, BNIP3, all members of the Bcl-2 family, and FasL, CARD11, Cytochrom c, p53; and some others belonging to anti-apoptotic subgroup: BIRC4, and IEX-1. This clear apoptotic transcriptional profile was unexpected because HVEM was described until yet as a costimulatory receptor and the pro-apoptotic effect of LIGHT was known to be mediated only by LTβR.

To address if this apoptotic transcriptional profile was correlated with a functional effect in vitro, we cultured B-CLL cells with LIGHT-transfected cells or with HVEM mAb, and both effectively increased the Annexin V+ cells. Furthermore, other observations in the laboratory confirmed that the pro-apoptotic effect of LIGHT on B-CLL cells was mediated through its interaction with HVEM, as demonstrated by:

1) the inability of rhLTα$_1$β$_2$, the other LTβR ligand, to induce CLL cell death, 2) B-CLL cells which did not express LTβR were nevertheless killed by anti-HVEM mAb, and 3) another B cell lymphadenopathy, mantle cell lymphoma, which is also negative for the expression of LTβR was killed by treatment with LIGHT (data not shown). This direct killing effect of HVEM on a lymphoid malignancy had never been described.

HVEM belongs to the subgroup of TNFR molecules, such as CD40 and CD30, that do not contain a death domain (DD) and are primarily involved in cell survival and costimulatory responses. Indeed, most of the TNFR family members implicated in apoptosis such as Fas, DR4, DR5, induce caspase signaling through their intracytoplasmic DD. However, it now appears clear that the TNFR members that do not contain a death domain can also induce cell death. For example, CD27 induced apoptosis of a Burkitt's lymphoma cell line, CD30 was involved in cell death signaling for thymic negative selection, CD40 ligation caused apoptotic cell death in transformed cells of mesenchymal and epithelial origin, and LIGHT induced cell death in some adenocarcinoma through interaction with LTβR. Our results include HVEM in this subgroup. Nevertheless, the absence of death domain complicated the understanding of the pathways implicated in HVEM. Then we performed different analysis to characterize the death mechanism induced through HVEM in CLL.

Two major apoptotic pathways have been identified: intrinsic and extrinsic pathways that can be distinguished by a prominent role for the mitochondria in the former, and activation of death receptors and caspase-8 in the latter pathway. We found that HVEM stimulation induced activation of caspase-3, -8 and -9. Pre-incubation of B-CLL cells with the pan-caspase inhibitor Z-VAD-FMK totally abrogated caspase-3 activation, but not cell death, suggesting the involvement of a mechanism independent of caspases. Moreover, HVEM stimulation decreased mitochondrial membrane potential and induced an upregulation of the pro-apoptotic Bax protein expression. In contrast, the anti-apoptotic Bcl-2 protein was unaltered. The mitochondrial activity has been shown to be strictly controlled by the balance between these Bcl-2 family members. In addition, the loss of membrane potential was not blocked by the pan-caspase inhibitor Z-VAD-FMK, suggesting that this step was independent of caspase activation. The upregulation of Bax could be associated with the loss of mitochondrial potential observed and together these results suggest an implication of the intrinsic apoptotic pathway. HVEM-mediated apoptosis was thus apparently involved in both the death receptor pathway (activation of caspase-8) and the mitochondria pathway (decreased mitochondrial membrane potential and upregulation of Bax). Also, since caspase-8 and caspase-9 were activated at approximately the same time, the death receptor pathway and the mitochondrial pathway are possibly parallel pathways in B-CLL cells stimulated via HVEM. Altogether, these data suggests that HVEM-induced cell death involved on one hand the activation of caspases, in an apoptotic mechanism; and on the other hand a pathway independent of caspases.

The two receptors of LIGHT apparently induce cell death through distinct mechanisms. Upon binding with LIGHT, LTβR recruited several TNFR-associated factors (TRAFs), which are coupling adaptors to trigger multiple signaling cascades. Further study has indicated that TRAF3 coupling is primarily involved in mediating LTβR-induced cell death; whereas TRAF2 and TRAF5 association play an important role in the activation of NF-κB. Proapoptotic features through LTβR differed from our observations on HVEM, since LTβR cell death did not cause caspase activation in HT29 colon cancer cells. Moreover, even through extensive caspase activation was observed on MDA-MB-231 breast cancer cells, LIGHT-mediated apoptosis seemed to be caspase-independent. Decreased mitochondrial membrane potential was observed in both cases. LIGHT-induced tumor cell death required the sensitization by IFNγ, which was not necessary in our experiments on B-CLL cells, thus suggesting distinct mechanisms for the pro-apoptotic pathways of both receptors.

Of note, the HVEM-induced CLL cell death compared favorably with that of the pan-B cell therapeutic mAb rituximab. Consequently HVEM could enhance efficacy of therapeutic agents, such as fludarabine, as it was demonstrated for rituximab and alemtuzumab monoclonal antibodies.

Others studies found that pre-activation with CD40L could sensitize B-CLL cells to the FasL and TRAIL-mediated apoptosis. Moreover, a cooperation between CD40L and LIGHT has been observed for dendritic cell maturation, LIGHT protein induction at the surface of B lymphocytes, or B-cell proliferation. These data prompted us to analyze whether CD40L could increase or block HVEM-mediated cell death, but we failed to detect any effect of CD40L pre-activation (data not shown). Interestingly, these observations suggest that activated B-CLL present in secondary lymphoid organs, which are activated cells, could also be killed by HVEM treatment.

Here, our data shows that LIGHT or anti HVEM antibodies could induce cell death of a B lymphoid malignancy directly through HVEM, in part through an apoptotic pathway and in part by a necrotic mechanism. This affects caspase activation, mitochondrial membrane potential and upregulation of pro-apoptotic proteins. Our results strongly suggested the involvement of TRAIL in HVEM-induced cell death. Aside this newly identified role of HVEM, LIGHT also induced chemokine release directly by leukemic cells, through HVEM. This latter event would be expected to play a key role in the recruitment of cells of the innate (NK cells, monocytes) and adaptive (T cells) immune systems, which in turn may be expected to exert additional controls on B-CLL cells (cf. FIG. 7). LIGHT-HVEM signalling represents a novel therapeutic target for cancer therapy. Soluble LIGHT or anti-HVEM mAb presents the attractive advantage of combining direct killing of malignant lymphocytes expressing HVEM by mechanisms such as induction of apoptosis, with the recruitment of immune effector cells through the production of chemokines.

Example 2

Characterization of Anti-HVEM mAb Clones mAbs:

BALB/c mice were immunised by IP injection of human HVEM-Ig fusion protein, after the last injection the spleen cells were fused with X63Ag8 myeloma cells according to standard procedures. The hybridoma supernatants were screened by cell surface staining of human HVEM cells lines.

Fourteen mAb clones were characterized for a number of methods including: i) typing of the mouse immunoglobulin heavy and light chain types, ii) flow cytometry analysis for binding cell surface HVEM and determination of mean fluorescent intensity (MFI) values, maximum saturation binding, and 50% saturation binding ($EC_{50}$ value), iii) competitive blocking studies with LIGHT, BTLA and HSV-gD, iv) mutagenesis analysis through binding of mAbs to a panel of HVEM mutants, and v) the ability of the mAb to induce apoptosis of CLL cells. Based on criteria from the competitive blocking and mutagenesis experiments, six epitope clusters were identified as epitopes I, II, III, IV, V and VI. The data represented in Table 2 is a summary subset for 3 mAbs.

Example 3

HVEM is Expressed in Hematogical Malignancies

Flow cytometry analysis shows that HVEM is expressed as determined on B-cell lymphoid neoplasm (see FIG. 8) as well as T-cell lymphoid neoplasms, non-Hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm and myeloid cell lineage neoplasm (data not shown).

Specimens of the different leukemias myeloma and myeloma were frozen and tested by flow cytometry for the cell surface expression of HVEM. Data are expressed as fold mean fluorescence intensity in comparison to negative control. CLL correspond to chronic B cell leukemia, ALL to acute lymphocytic leukemia, MM to multiple myeloma cells, MCL to mantle cell lymphoma, FL to follicular lymphoma and diffuse LBCL to diffuse large B cell lymphoma.

Example 4

HVEM Triggering Induces B Cell Death

HVEM signalling is associated with the cell death of various B cell hematological malignancies (cf. example 3). We tested whether HVEM stimulation could also induce normal B cells death.

PBMC from healthy donors were isolated on Ficoll-Hypaque gradients (Amersham Biosciences, Saclay, France). B lymphocytes were isolated as the CD19+ PBMC population using the MACS CD19 Microbeads isolation kit (Miltenyi Biotec, Bergisch Gladbach, Germany), following manufacturer's recommendation. The purity of the preparation was checked by flow cytometry analysis, and was >98% in all experiments (data not shown).

B lymphocytes were treated or not with 30 µg/ml anti-HVEM monoclonal antibody (mAb) (SmithKline Beecham) for 24 hours. Then, cells were collected and cell death was analyzed by Annexin V-Cy5 (BD Biosciences) and Propidium Iodide (PI) double staining (BD Biosciences). Briefly, $5 \times 10^5$ cells were washed once with phosphate-buffered saline (PBS) 1% FCS and resuspended in 100 µl 1× binding buffer (BD Biosciences) with 5 µl Annexin V-Cy5 for 10 min at room temperature in the dark. Then 200 µl of 1× binding buffer and 3.5 µl of PI were added, and cells were incubated for 5 min at RT in the dark. Cells were then analyzed on a FACSCanto cytometer (Becton Dickinson). Data analysis was performed with FACSDiva software (Becton Dickinson). Dead cells were measured as the percentage of Annexin V and PI double positive cells.

As shown in FIG. 9, normal B cells were sensitive to HVEM triggering which elicited death of normal B cells.

This observation is interesting since B cells are now known as important targets for the treatment of autoimmune diseases (AID) as evidenced by the therapeutic utility demonstrated for CD20 mAbs in diseases such as rheumatoid arthritis. Interestingly, despite the fact that CD20 mAbs are weak inducers of B cells death, they nevertheless have been used effectively for the treatment of autoimmune diseases. Hence, the properties that we have identified for HVEM in normal B cells make HVEM an attractive target for use in the treatment of AID. Ligands of HVEM selected from the group consisting of LIGHT or a fragment of LIGHT which induces apoptosis in chronic lymphocytic leukemia B cells, an anti-HVEM antibody, and a fragment thereof which binds to HVEM may therefore be used for the treatment of autoimmune diseases.

REFERENCES

Throughout this application, various references describe the state of the art to which this invention pertains. The disclosures of these references are hereby incorporated by reference into the present disclosure.

Barbas C F, Bain J D, Hoekstra D M, Lerner R A. (1992), Semisynthetic combinatorial antibody libraries: a chemical solution to the diversity problem. PNAS USA, 89, 4457-4461.

Bonizzi, G. and M. Karin. The two NF-kappaB activation pathways and their role in innate and adaptive immunity. Trends Immunol, 2004. 25(6): p. 280-8.

Carfi, A., S. H. Willis, J. C. Whitbeck, C. Krummenacher, G. H. Cohen, R. J. Eisenberg, and D. C. Wiley. Herpes simplex virus glycoprotein D bound to the human receptor HveA. Mol Cell, 2001. 8(1): p. 169-79.

Chiorazzi, N., K. R. Rai, and M. Ferrarini. Chronic lymphocytic leukemia. N Engl J Med, 2005. 352(8): p. 804-15.

Collette, Y., A. Gilles, P. Pontarotti, and D. Olive. A co-evolution perspective of the TNFSF and TNFRSF families in the immune system. Trends Immunol, 2003. 24(7): p. 387-94.

Compaan, D. M., L. C. Gonzalez, I. Tom, K. M. Loyet, D. Eaton, and S. G. Hymowitz. Attenuating lymphocyte activity: the crystal structure of the BTLA-HVEM complex. J Biol Chem, 2005. 280(47): p. 39553-61.

Costello R T, Mallet F, Barbarat B, Schiano De Colella J M, Sainty D, Sweet R W, Truneh A, Olive D. Stimulation of non-Hodgkin's lymphoma via HVEM: an alternate and safe way to increase Fas-induced apoptosis and improve tumor immunogenicity. Leukemia. 2003 December; 17(12):2500-7.

Croft, M. Co-stimulatory members of the TNFR family: keys to effective T-cell immunity? Nat Rev Immunol, 2003. 3(8): p. 609-20.

Freireich, E. J. and N. Lemak. Milestones in Leukemia Research and Therapy. 1991, Baltimore: Johns Hopkins University Press.

Gonzalez, L. C., K. M. Loyet, J. Calemine-Fenaux, V. Chauhan, B. Wranik, W. Ouyang, and D. L. Eaton. A coreceptor interaction between the CD28 and TNF receptor family members B and T lymphocyte attenuator and herpesvirus entry mediator. Proc Natl Acad Sci USA, 2005. 102(4): p. 1116-21.

Granger, S. W. and S. Rickert. LIGHT-HVEM signaling and the regulation of T cell-mediated immunity. Cytokine Growth Factor Rev, 2003. 14(3-4): p. 289-96.

Harlow E. et al., Antibodies: A Laboratory Manual, Cold Spring Harbor Laboratory, New York, (1988).

Harrop, J. A., M. Reddy, K. Dede, M. Brigham-Burke, S. Lyn, K. B. Tan, C. Silverman, C. Eichman, R. DiPrinzio, J. Spampanato, T. Porter, S. Holmes, P. R. Young, and A. Truneh. Antibodies to TR2 (herpesvirus entry mediator), a new member of the TNF receptor superfamily, block T cell proliferation, expression of activation markers, and production of cytokines. J Immunol, 1998. 161(4): p. 1786-94.

Harrop, J. A., P. C. McDonnell, M. Brigham-Burke, S. D. Lyn, J. Minton, K. B. Tan, K. Dede, J. Spampanato, C. Silverman, P. Hensley, R. DiPrinzio, J. G. Emery, K. Deen, C. Eichman, M. Chabot-Fletcher, A. Truneh, and P. R. Young. Herpesvirus entry mediator ligand (HVEM-L), a novel ligand for HVEM/TR2, stimulates proliferation of T cells and inhibits HT29 cell growth. J Biol Chem, 1998. 273(42): p. 27548-56.

Harrop, J. A., M. Reddy, K. Dede, M. Brigham-Burke, S. Lyn, K. B. Tan, C. Silverman, C. Eichman, R. DiPrinzio, J. Spampanato, et al 1998. Antibodies to TR2 (herpesvirus entry mediator), a new member of the TNF receptor superfamily, block T cell proliferation, expression of activation markers, and production of cytokines. J. Immunol. 161: 1786.

Hauer, J., S. Puschner, P. Ramakrishnan, U. Simon, M. Bongers, C. Federle, and H. Engelmann. TNF receptor (TNFR)-associated factor (TRAF) 3 serves as an inhibitor of TRAF2/5-mediated activation of the noncanonical NF-kappaB pathway by TRAF-binding TNFRs. Proc Natl Acad Sci USA, 2005. 102(8): p. 2874-9.

Hsu, H., I. Solovyev, A. Colombero, R. Elliott, M. Kelley, and W. J. Boyle. ATAR, a novel tumor necrosis factor receptor family member, signals through TRAF2 and TRAF5. J Biol Chem, 1997. 272(21): p. 13471-4.

Jaffe, E. S., P. M. Banks, B. Nathwani, J. Said, and S. H. Swerdlow. Recommendations for the reporting of lymphoid neoplasms: A report from the Association of Directors of Anatomic and Surgical Pathology. Mod Pathol, 2004. 17(1): p. 131-5.

Kohler and Milstein (1975) Continuous cultures of fused cells secreting antibody of predefined specificity. Nature; 256, 495-7.

Kuppers, R. Mechanisms of B-cell lymphoma pathogenesis. Nat Rev Cancer, 2005. 5(4): p. 251-62.

Kwon, B. S., K. B. Tan, J. Ni, K. O. Oh, Z. H. Lee, K. K. Kim, Y. J. Kim, S. Wang, R. Gentz, G. L. Yu, J. Harrop, S. D. Lyn, C. Silverman, T. G. Porter, A. Truneh, and P. R. Young. A newly identified member of the tumor necrosis factor receptor superfamily with a wide tissue distribution and involvement in lymphocyte activation. J Biol Chem, 1997. 272(22): p. 14272-6.

Marsters, S. A., T. M. Ayres, M. Skubatch, C. L. Gray, M. Rothe, and A. Ashkenazi. Herpesvirus entry mediator, a member of the tumor necrosis factor receptor (TNFR) family, interacts with members of the TNFR-associated factor family and activates the transcription factors NF-kappaB and AP-1. J Biol Chem, 1997. 272(22): p. 14029-32.

Matsui, H., Y. Hikichi, I. Tsuji, T. Yamada, and Y. Shintani. LIGHT, a member of the tumor necrosis factor ligand superfamily, prevents tumor necrosis factor-alpha-mediated human primary hepatocyte apoptosis, but not Fas-mediated apoptosis. J Biol Chem, 2002. 277(51): p. 50054-61.

Mauri, D. N., R. Ebner, R. I. Montgomery, K. D. Kochel, T. C. Cheung, G. L. Yu, S. Ruben, M. Murphy, R. J. Eisenberg, G. H. Cohen, P. G. Spear, C. F. Ware. 1998. LIGHT, a new member of the TNF superfamily, and lymphotoxin are ligands for herpesvirus entry mediator. Immunity 8:21.

Montgomery, R. I., M. S. Warner, B. J. Lum, P. G. Spear. 1996. Herpes simplex virus-1 entry into cells mediated by a novel member of the TNF/NGF receptor family. Cell 87:427.

Morel, Y., J.-M. Schiano de Colella, J. Harrop, K. C. Deen, S. D. Holmes, T. A. Wattam, S. S. Khandekar, A. Truneh, R. W. Sweet, J. A. Gastaut, D. Olive, R. T. Costello. 2000. Reciprocal expression of the TNF family receptor HVEM and its ligand LIGHT on activated T cells: LIGHT down-regulates its own receptor. J. Immunol. 165:4397.

Morel, Y., A. Truneh, R. W. Sweet, D. Olive, and R. T. Costello. The TNF superfamily members LIGHT and CD154 (CD40 ligand) costimulate induction of dendritic cell maturation and elicit specific CTL activity. J Immunol, 2001. 167(5): p. 2479-86.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Nakano, H., H. Oshima, W. Chung, L. Williams-Abbott, C. F. Ware, H. Yagita, and K. Okumura. TRAF5, an activator of NF-kappaB and putative signal transducer for the lymphotoxin-beta receptor. J Biol Chem, 1996. 271(25): p. 14661-4.

Neuberger M S, Williams G T, Fox R O. Recombinant antibodies possessing novel effector functions. Nature. 1984 Dec. 13-19; 312(5995):604-8.

Olive D., Raymond J., Dubreuil P., Charmot D., Jacques Y., Mawas C. Anti-Interleukin 2 receptor monoclonal antibodies. Respective role of epitope mapping and monoclonal antibody-receptor interactions in their antagonist effects on interleukin 2-dependent T cell growth. Eur J Immunol 1986; 16: 611-616.

Pomerantz, J. L. and D. Baltimore. Two pathways to NF-kappaB. Mol Cell, 2002. 10(4): p. 693-5.

Riechmann L, Clark M, Waldmann H, Winter G Reshaping human antibodies for therapy. Nature. 1988 Mar. 24; 332 (6162):323-7.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Rooney, I. A., K. D. Butrovich, A. A. Glass, S. Borboroglu, C. A. Benedict, J. C. Whitbeck, G. H. Cohen, R. J. Eisenberg, C. F. Ware. 2000. The lymphotoxin-receptor is necessary and sufficient for LIGHT-mediated apoptosis of tumor cells. J. Biol. Chem. 275:14307.

Sedy, J. R., M. Gavrieli, K. G. Potter, M. A. Hurchla, R. C. Lindsley, K. Hildner, S. Scheu, K. Pfeffer, C. F. Ware, T. L. Murphy, and K. M. Murphy. B and T lymphocyte attenuator regulates T cell activation through interaction with herpesvirus entry mediator. Nat Immunol, 2005. 6(1): p. 90-8.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Stewart, B. W. and P. Kleihues, eds. World Cancer Report. 2003, WHO—International Agency for Research on Cancer Press: Lyon. 351 pp.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6):805-14.

Tamada, K., K. Shimozaki, A. I. Chapoval, Y. Zhai, J. Su, S. F. Chen, S. L. Hsieh, S, Nagata, J. Ni, L. Chen. 2000. LIGHT, a TNF-like molecule, costimulates T cell proliferation and is required for dendritic cell-mediated allogeneic T cell response. J. Immunol. 164:4105.

Tan, K. B., J. Harrop, M. Reddy, P. Young, J. Terrett, J. Emery, G. Moore, and A. Truneh. Characterization of a novel TNF-like ligand and recently described TNF ligand and TNF receptor superfamily genes and their constitutive and inducible expression in hematopoietic and non-hematopoietic cells. Gene, 1997. 204(1-2): p. 35-46.

Wallach, D. TNF ligand and TNF/NGF receptor families, in Cytokine Reference, J. J. Oppenheim and M. Feldmann, Editors. 2001, Academic Press: London. p. 377-411.

Wallach, D., E. E. Varfolomeev, N. L. Malinin, Y. V. Goltsev, A. V. Kovalenko, and M. P. Boldin. Tumor necrosis factor receptor and Fas signaling mechanisms. Annu Rev Immunol, 1999. 17: p. 331-67.

Waterhouse P, Griffiths A D, Johnson K S, Winter G. (1993) Combinatorial infection and in vivo recombination: a strategy for making large phage antibody repertoires. Nucleic Acids Research, 21, 2265-2266.

Watts, T. H. TNF/TNFR family members in costimulation of T cell responses. Annu Rev Immunol, 2005. 23: p. 23-68.

Whitbeck, J. C., C. Peng, H. Lou, R. Xu, S. H. Willis, M. Ponce de Leon, T. Peng, A. V. Nicola, R. I. Montgomery, M. S. Warner, A. M. Soulika, L. A. Spruce, W. T. Moore, J. D. Lambris, P. G. Spear, G. H. Cohen, and R. J. Eisenberg. Glycoprotein D of herpes simplex virus (HSV) binds directly to HVEM, a member of the tumor necrosis factor receptor superfamily and a mediator of HSV entry. J Virol, 1997. 71(8): p. 6083-93.

Ye, Q., C. C. Fraser, W. Gao, L. Wang, S. J. Busfield, C. Wang, Y. Qiu, A. J. Coyle, J. C. Gutierrez-Ramos, and W. W. Hancock. Modulation of LIGHT-HVEM costimulation prolongs cardiac allograft survival. J Exp Med, 2002. 195 (6): p. 795-800.

Yu, K. Y., B. Kwon, J. Ni, Y. Zhai, R. Ebner, B. S. Kwon. 1999. A newly identified member of tumor necrosis factor receptor superfamily (TR6) suppresses LIGHT-mediated apoptosis. J. Biol. Chem. 274:13733.

Zhai, Y., R. Guo, T. L. Hsu, G. L. Yu, J. Ni, B. S. Kwon, G. W. Jiang, J. Lu, J. Tan, M. Ugustus, et al 1998. LIGHT, a novel ligand for lymphotoxin receptor and TR2/HVEM, induces apoptosis and suppresses in vivo tumor formation via gene transfer. J. Clin. Invest. 102:1142.

The invention claimed is:

1. A method for treating hematologic malignancies comprising the step of administering to a patient an effective amount of a ligand of HVEM,
wherein said ligand of HVEM is a monoclonal antibody selected from the group consisting of:
(i) a monoclonal antibody that does not bind to an HVEM mutant in which cysteine rich domain 1 (CRD1) of HVEM is deleted (CRD1 deletion mutant) but is affected by an HVEM mutant in which amino acid residues 129-133 within cysteine rich domain 3 of HVEM have been deleted (del129-133 deletion mutant) and blocks the binding of HVEM to LIGHT, not the binding of HVEM to BTLA or HSV-gD;
(ii) a monoclonal antibody that that does bind to an CRD1 deletion mutant but not to the del129-133 deletion mutant, or an HVEM mutant in which an alanine substitution of amino acid residues 131-133 of HVEM has been made (mut131-133 mutant);

(iii) a monoclonal antibody that does not bind to the CRD1 deletion mutant and is not affected by the del129-133deletion mutant , and does not inhibit the binding of HVEM to LIGHT, BTLA or HSV-gD;

(iv) a monoclonal antibody that is not affected by the CRD1 deletion mutant but is affected by the del129-133 deletion mutant, and does not inhibit the binding of HVEM to LIGHT, BTLA or HSV-gD;

(v) a monoclonal antibody that does bind to the CRD1 deletion but not to the del129-133 deletion mutant, is not affected by the mut131-133 mutant, and is not able to block HVEM binding to LIGHT, BTLA or HSV-gD; and (vi) a monoclonal antibody that does bind to the CRD1 deletion mutant but is affected in part by the del129-133deletion mutant, or by the mut131-133 mutant, and is able to block HVEM binding to LIGHT, BTLA and HSV-gD, and said monoclonal antibody induces apoptosis in a malignant lymphocyte.

2. The method according to claim 1, wherein said monoclonal antibody is obtainable from a hybridoma deposited at the COLLECTION NATIONALE DE CULTURES DE MICROORGANISMES (CNCM) selected from the group consisting of CNCM I-3752, CNCM I-3753 and CNCM I-3754.

* * * * *

UNITED STATES PATENT AND TRADEMARK OFFICE
CERTIFICATE OF CORRECTION

| | | |
|---|---|---|
| PATENT NO. | : 8,318,166 B2 | Page 1 of 1 |
| APPLICATION NO. | : 12/602539 | |
| DATED | : November 27, 2012 | |
| INVENTOR(S) | : Daniel Olive et al. | |

It is certified that error appears in the above-identified patent and that said Letters Patent is hereby corrected as shown below:

In claim 1, column 36, line 63, please delete "CDR1" and insert -- CRD1 --

Signed and Sealed this
Twenty-ninth Day of January, 2013

David J. Kappos
*Director of the United States Patent and Trademark Office*

```
                        SEQUENCE LISTING

<160> NUMBER OF SEQ ID NOS: 1

<210> SEQ ID NO 1
<211> LENGTH: 25
<212> TYPE: PRT
<213> ORGANISM: Artificial
<220> FEATURE:
<223> OTHER INFORMATION: epitope

<400> SEQUENCE: 1

Cys Pro Lys Cys Ser Pro Gly Tyr Arg Val Lys Glu Ala Cys Gly Glu
1               5                   10                  15

Leu Thr Gly Thr Val Cys Glu Pro Cys
            20                  25
```